United States Patent
Krupka et al.

(10) Patent No.: US 7,169,613 B2
(45) Date of Patent: Jan. 30, 2007

(54) METHOD FOR AVOIDING THE CONTAMINATION OF NEGATIVE SAMPLING MATERIAL BY SAMPLES CONTAINING ANALYTES DURING THE USE OF AUTOMATIC PIPETTE MACHINES

(75) Inventors: Udo Krupka, Marburg (DE); Wolfgang Schmandt, Pohlheim (DE)

(73) Assignee: Dade Behring Marburg GmbH, Marburg (DE)

( * ) Notice: Subject to any disclaimer, the term of this patent is extended or adjusted under 35 U.S.C. 154(b) by 334 days.

(21) Appl. No.: 10/451,326

(22) PCT Filed: Dec. 21, 2001

(86) PCT No.: PCT/EP01/15197

§ 371 (c)(1),
(2), (4) Date: Jun. 20, 2003

(87) PCT Pub. No.: WO02/49764

PCT Pub. Date: Jun. 27, 2002

(65) Prior Publication Data

US 2004/0063185 A1    Apr. 1, 2004

(30) Foreign Application Priority Data

Dec. 21, 2000    (DE) ................ 100 64 428

(51) Int. Cl.
*C12Q 1/34* (2006.01)
*G01N 35/08* (2006.01)
*C12M 1/36* (2006.01)

(52) U.S. Cl. ............... 436/43; 436/55; 435/286.4; 435/286.5

(58) Field of Classification Search ........... 436/43, 436/47, 49; 435/286.4, 286.5; 422/54, 65, 422/100
See application file for complete search history.

(56) References Cited

U.S. PATENT DOCUMENTS

| | | | |
|---|---|---|---|
| 5,061,639 A | * | 10/1991 | Lung et al. ............ 436/164 |
| 5,447,838 A | * | 9/1995 | Meiklejohn et al. ....... 435/5 |
| 5,538,849 A |   | 7/1996 | Hiroaki et al. |
| 5,610,069 A | * | 3/1997 | Clark et al. ............ 436/49 |
| 5,635,364 A | * | 6/1997 | Clark et al. ............ 435/7.92 |

FOREIGN PATENT DOCUMENTS

| | | |
|---|---|---|
| EP | 0 733 905 A | 9/1996 |
| WO | WO 99/25476 A | 5/1999 |
| WO | WO 00/05580 A | 2/2000 |

OTHER PUBLICATIONS

Schmidt et al. Metabolites: A Helping Hand for Pathway Evolution?; Trends in Biochmical Sciences, vol. 28, No. 6 (2003) pp. 336-341.*

* cited by examiner

*Primary Examiner*—Terry McKelvey
*Assistant Examiner*—Paul Martin
(74) *Attorney, Agent, or Firm*—Finnegan, Henderson, Farabow, Garrett and Dunner, L.L.P.

(57) ABSTRACT

The invention relates to a method for reducing the contamination of reaction containers which are empty or already fitted with analyte-free sampling material or sampling material having a low analyte concentration, inside a configuration of reaction containers which are spatially close to each other, when pipetting samples or reagents using an automatic sample distributor. The invention also relates to hardware-related measures for reducing or avoiding possible contamination.

6 Claims, 10 Drawing Sheets

Figure 1:
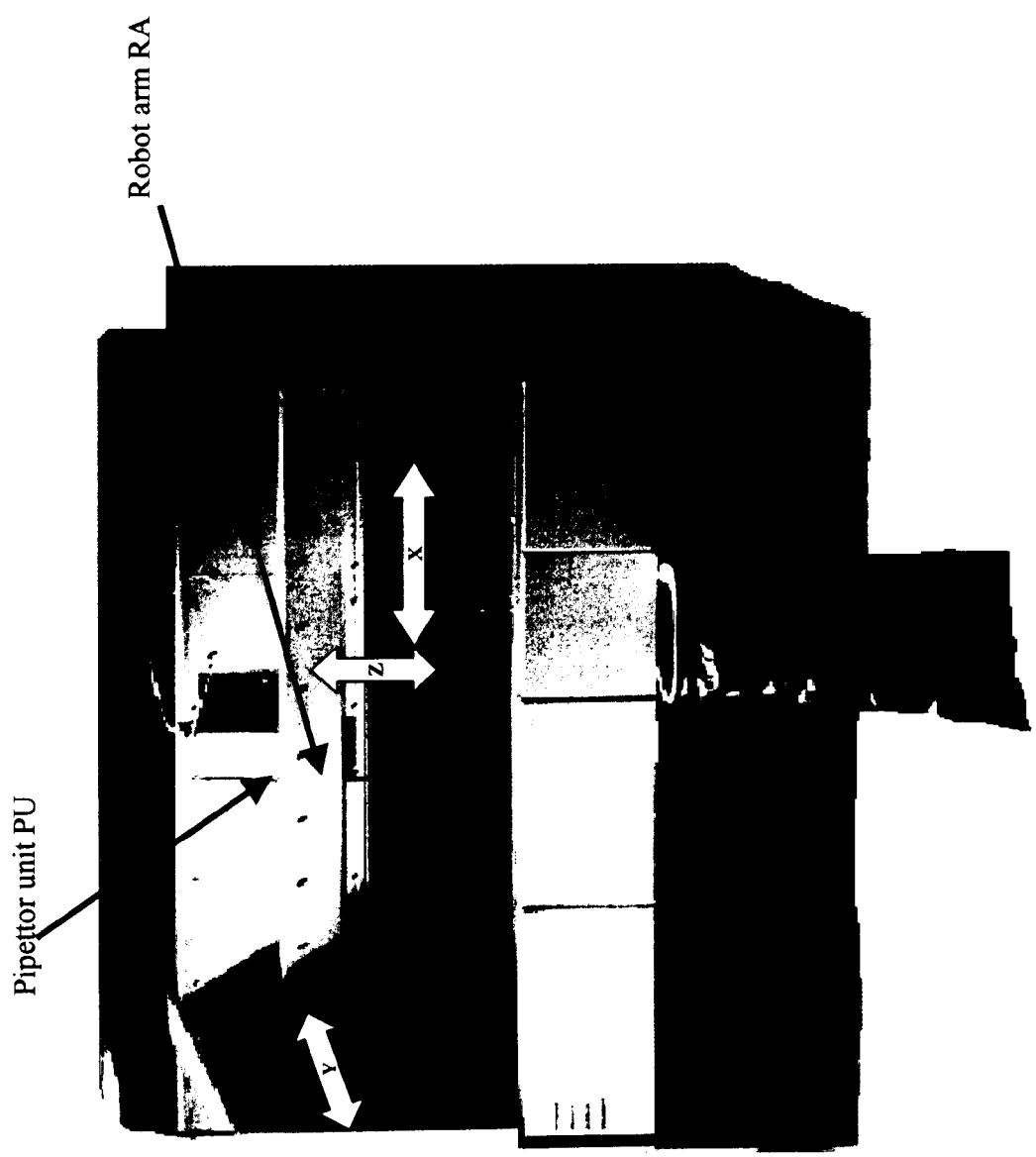

Fig. 3: BEP 2000 processes
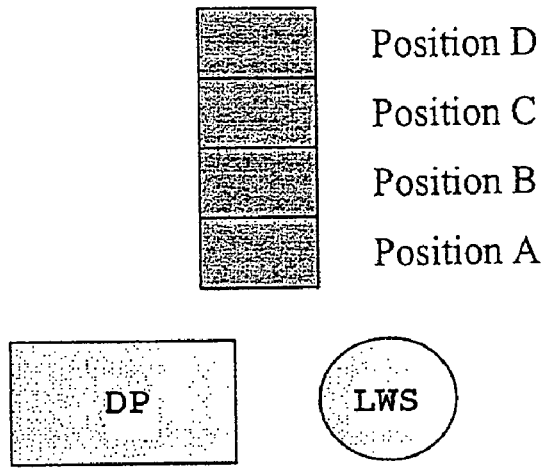
Fig. 4: Well positions on the MTP
Strips:     1  2  3  4  5  6  7  8  9  10  11  12
         A
         B
         C
         D
Rows:    E
         F
         G
         H

Fig. 5

| System | Incubators | Colorimeter | Luminometer | Pipette | Sample Rack | Washer | Plate Transport | Reminders |

Options
Syringe volume: 1000 ul
☑ Disposable tips
☑ Enable clot detection
☑ Enable liquid level detection

Dilution Plates
Coordinates: mtpdil2.mpc
Maximum Volume: 460 ul
Minimum Volume: 115 ul

Dilution Tubes
Max. Volume: 10000 ul
Min. Volume: 100 ul

Information
Firmware version: ?

[Upgrade Firmware]

Aspirate Profile
Profile number: 0
Description: Multi Disp Asp
Start velocity: 500 Hz
Top velocity: 1000 Hz
Acceleration: 2 x2.5 kHz/s
Airgap: 0 ul Dive out velocity: 10 %
Dive out: 400 Steps
Submerge steps: 0 Steps
LLD Speed: 100 %
Transportation airgap: 10 ul
Aspirate delay: 5 x0.1s

Active washing
Dive out velocity: 5 %
Dive out: 500 Steps

Dispense Profile
Profile number: 3
Description: Med Vol 50ul-300ul
Start velocity: 800 Hz
Top velocity: 2000 Hz
Acceleration: 20 x2.5 kHz/s
Cutoff velocity: 2000 Hz
Dive out velocity: 10 %
Dive out: 500 Steps
Resoak: 20 ul
Dispense delay: 2 x0.1s

Fig. 7

| System | Incubators | Colorimeter | Luminometer | Pipette | Sample Rack | Washer | Plate Transport | Reminders |

Options
Syringe volume: 1000 ul
☑ Disposable tips
☑ Enable clot detection
☑ Enable liquid level detection Dilution Plates
Coordinates: mtpdil2.mpc
Maximum Volume: 460 ul
Minimum Volume: 115 ul Dilution Tubes
Max. Volume: 10000 ul
Min. Volume: 100 ul Information
Firmware version ?

Upgrade Firmware

Aspirate Profile
Profile number: 0
Description: Multi Disp Asp
Start velocity: 500 Hz
Top velocity: 1000 Hz
Acceleration: 2 x2.5 kHz/s
Airgap: 0 ul Dive out velocity: 10 %
Dive out: 400 Steps
Submerge steps: 0 Steps
LLD Speed: 100 %
Transportation airgap: 10 ul
Aspirate delay: 5 x0.1s Dispense Profile
Profile number: 6
Description: Versuch2
Start velocity: 400 Hz
Top velocity: 900 Hz
Acceleration: 5 x2.5 kHz/s
Cutoff velocity: 900 Hz
Dive out velocity: 1 %
Dive out: 500 Steps
Resoak: 20 ul
Dispense delay: 2 x0.1s Active washing
Dive out velocity: 5 %
Dive out: 500 Steps OK | Discontinue | help

Fig. 9

| System | Incubators | Colorimeter | Luminometer | Pipette | Sample Rack | Washer | Plate Transport | Reminders |

Options
Syringe volume: 1000 ul
☑ Disposable tips
☑ Enable clot detection
☑ Enable liquid level detection Dilution Plates
Coordinates: mtpdl2.mpc
Maximum Volume: 460 ul
Minimum Volume: 115 ul Dilution Tubes
Max. Volume: 10000 ul
Min. Volume: 100 ul Information
Firmware version: ?

Upgrade Firmware

Aspirate Profile
Profile number: 5
Description: Versuch1
Start velocity: 200 Hz
Top velocity: 300 Hz
Acceleration: 2 x2.5 kHz/s
Airgap: 0 ul Dive out velocity: 1 %
Dive out: 400 Steps
Submerge steps: 0 Steps
LLD Speed: 100 %
Transportation airgap: 10 ul
Aspirate delay: 5 x0.1s Dispense Profile
Profile number: 6
Description: Versuch2
Start velocity: 900 Hz
Top velocity: 900 Hz
Acceleration: 5 x2.5 kHz/s
Cutoff velocity: 900 Hz
Dive out velocity: 1 %
Dive out: 500 Steps
Resoak: 20 ul
Dispense delay: 2 x0.1s Active washing
Dive out velocity: 5 %
Dive out: 0 Steps Fig. 10: Example of a covering
(Transverse section/view from above)
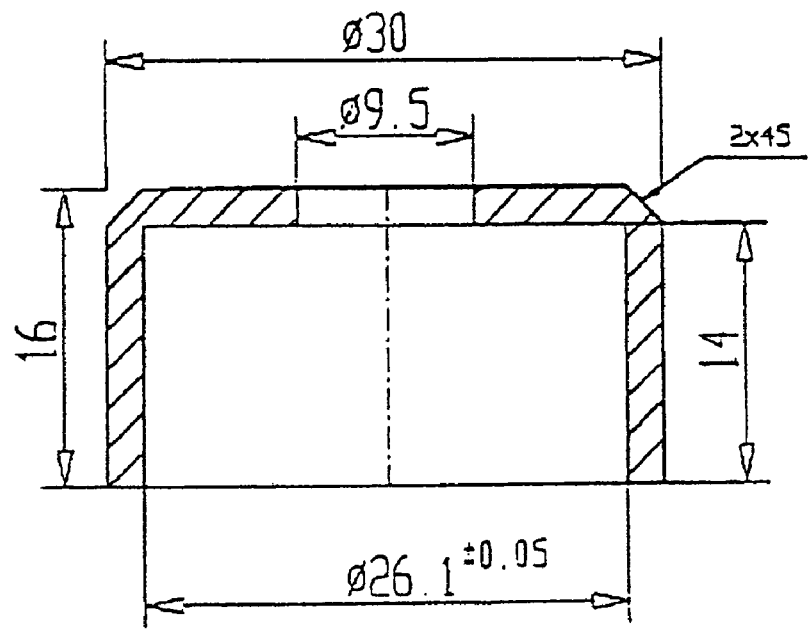
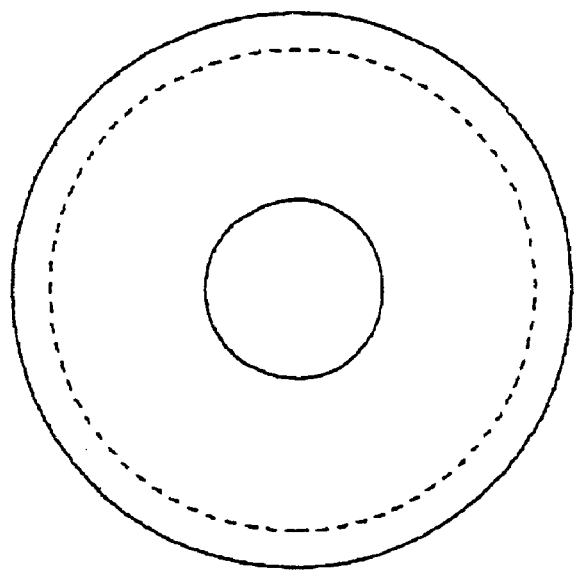

METHOD FOR AVOIDING THE CONTAMINATION OF NEGATIVE SAMPLING MATERIAL BY SAMPLES CONTAINING ANALYTES DURING THE USE OF AUTOMATIC PIPETTE MACHINES

The invention relates to methods for reducing the contamination of empty reaction vessels, or reaction vessels which are already charged with analyte-free sample material or sample material which contains a low concentration of analyte, within an arrangement of reaction vessels which are in spatial proximity to each other while samples or reagents are being pipetted using an automated sample dispenser, and also to hardware-side measures for reducing or preventing contaminations.

The invention was derived using the Dade Behring BEP® 2000, which was also used to work out the examples, without, however, restricting the subject matter of the present invention to this system.

The automated pipetting of samples by means of what are termed pipetting robots (also called sample dispensers) is employed widely in laboratories for human serology and veterinary investigation establishments and is used for diagnostic investigations and, recently, in connection with microbiological/recombinant DNA problems as well.

Commercial instruments which have been specially developed for sample pipetting purposes, i.e. stand-alone instruments, such as the Hamilton Microlab AT Plus®, are used for this purpose while the tests are worked through separately and manually or using processors, such as the Dade Behring BEP III®, which are specially designed for the purpose.

Alternatively, the sample dispensing is an integral part, or a module, of a fully automated machine which also automatically performs the actual test method for the analyte to be determined which follows.

Examples of these so-called front-end instruments are:
BN 100®, from Dade Behring Marburg GmbH for performing immunochemical plasma protein determinations on human sample material;
ETI Lab®, from DiaSorin, and BEP® 2000, from Dade Behring, for detecting analytes in the field of infection serology, based on enzyme-linked immunosorbent assays (ELISAs).

While the investigation methods and the diagnostic applications of the two products mentioned differ substantially, the logic on which the two types of instrumentation are based is identical. The given fully automated machine dispenses the samples undiluted, or after a preliminary dilution, into reaction vessels in which the actual determination method is likewise carried out automatically by adding immunologically reactive components.

In a general manner, small tubes, microtitration plates, cuvettes or the like can be used as reaction vessels.

After the test result has been measured (photometrically, turbidimetrically or the like), each individual sample is classified, by programmed computer programs in the relevant software, while applying criteria for validating the entire test run, as being positive, negative or, if provided in the test definition, threshold, in relation to the analyte being investigated.

Analytes can be: specific plasma proteins (for example tumor markers), fertility or thyroid gland markers (for example FSH or Ca 15-9), antibodies (for example G class rubella-specific immunoglobulins), antigens (for example hepatitis B surface antigen/HBsAg) and other parameters known to the skilled person.

In the case of certain parameters, it is diagnostically important, for indicating or monitoring therapy, to also determine the concentration quantitatively or semiquantitatively, with this as a rule also taking place in a software-supported manner. Frequently, the patient-oriented result printout (computer belonging to the analyteal instrument, hard copy and/or central computer) is assigned to the corresponding sample by the primary tube being detected by way of a bar code.

If, during the pipetting process, empty reaction vessels, or reaction vessels which have already been charged with analyte-free sample material, are in fact contaminated with analyte-containing material, such traces can erroneously simulate reactivity in samples which are in fact analyte-free. Contamination can likewise lead to parameter levels which are too high being simulated in samples which contain low analyte concentrations.

The possible consequences of such a falsely positive reaction are manifold and known, with it being possible for such effects to have particularly serious consequences in the field of infection serology:

an entirely nonexistent immunological protection could be simulated; a falsely positive result when determining antibodies directed against hepatitis A virus antigen (anti-HAV) or hepatitis B virus antigen (anti-HBs) could lead to failure to perform a vaccination which should rightly have been carried out;

when screening parameters in connection with blood donation, a high proportion of falsely positive results would substantially delay the release of the stored blood, since it would be necessary to carry out further tests; although it is to be assumed that, as a rule, no harm would come to the stored blood recipients, it would result in a considerable increase in time consumption and expenditure, apart from possible psychological irritation caused to the relevant donors if the latter had to be summoned once again for the purpose of clearing up the ambiguity in the event of a falsely positive AIDS finding (anti-HIV);

in the case of quantitative determinations, for example of tumor markers using BN 100® or anti-rubella virus antibodies using ETILab®, it would be possible to conceive of incorrect conclusions being drawn with regard to the therapy employed (progress of tumor markers in patients under therapy) or measures to be initiated (falsely positive increase in rubella-specific antibodies within the context of monitoring pregnancy).

Both the effects of contamination and the possible consequences are known under a variety of terms and have been countered with a very wide variety of measures, which are known to the skilled person, in order to make laboratory diagnostics more reliable and, not least, to save time and expenditure for the user:

"Entrainment" or "carry-over" is, for example, understood generally as meaning analyte residues which adhere to the inner surface of pipetting tips or needles; when needle tips, for example, are used for the duration of the sample pipetting operation, very small residues of analyte-containing sample can be carried over in one or even several of the subsequent operations for pipetting samples which do not contain this analyte or only contain it at low concentration. The consequence of such an effect can then be recognized by the fact that falsely positive reactivities are measured in one or even several of the reaction vessels which, during the pipetting, were located chronologically, and usually also physically, after the position of the analyte-containing sample. When several reaction vessels are affected one after the other, the degree to which this effect is expressed typically declines systematically from one reaction vessel to the next.

Thus far, an effective countermeasure is regarded as having been implemented when a carry-over of 1 millionth part ($1:10^6$ final dilution of the analyte-containing sample in analyte-free sample) can no longer be detected, as interfering experimentally in the test method employed, in the first position following the analyte-containing sample.

At present, this can be achieved by using suitable washing buffer solutions, which are employed, for example, to rinse the pipetting needles (frequently stainless steel needles) after each pipetting operation in order to remove analytes, which may be adhering to the inner surface of the needles, before the next sample is pipetted (example: Tecan Genesis RSP®).

Alternatively, use is made of disposable tips, with these parts, which are also termed exchangeable tips, being discarded after each sample-pipetting operation (example: Sorin ETILab® and Dade Behring BEP® 2000). This thereby achieves complete freedom from entrainment.

An entirely different form of contamination is brought about by analyte-containing sample material which, after the sample material has been taken up, is located on the outer wall of permanent tips or exchangeable tips and can drip off when the pipettor (pipetting unit) is moved over empty or filled reaction vessels. This leads to similar falsely positive results as are obtained in connection with the abovementioned carry-over effect. However, by contrast, it is not possible, in this case, to detect any systematic clustering at particular positions.

As state of the art, an effective countermeasure is regarded as having been implemented when such dripping can no longer be detected optically in experimental operations in which highly concentrated dye solutions are pipetted. This is typically carried out by means of numerous pipetting operations at several positions or, ideally, over all conceivable locations of reaction vessels (when wells in microtitration plates are used as the reaction vessels, over the entire plate and relating to all the positions in the microtitration plate).

At present, improvements are achieved either using absorbent paper, which is punched through by the pipette tip in order to wipe away sample material which is adhering to the outer surface (Hamilton Microlab AT Plus®), or by programming dwell times for the pipettor (Dade Behring BEP® 2000) and/or regulating the velocity of the mechanical movement of the pipettor unit (Tecan DITI 200 AC/C®).

Finally, it is also possible to use liquid detection (by means of ultrasound or capacitively) to ensure that the tip is only immersed to a short depth in sample material. Immersion depths of only a few tenths of a millimeter effectively reduce the carry-over of liquid residues on the outside of the tips (for example Canberra Packard Multiprobe® Systems).

Despite these effects, which are known to the skilled person, and the possible countermeasures, it is still possible, in accordance with the prior art, for occasional falsely positive reactions to occur, with these reactions being produced by an entirely different effect:

both when using permanent needles and when using exchangeable tips, analyte-containing sample material can slop or spray over into adjacent reaction vessels.

Such effects, which are termed spill-over effects, occur sporadically when there are particular differences in the geometry of the reaction vessels and/or the exchangeable tips as disposable articles: it can then happen that, with the given delivery characteristics of the pipettor unit, the sample jet is physically delivered so inappropriately that small droplets "slop over" from the designated reaction wells into adjacent reaction vessels. This effect is typically restricted to the immediate environment of the position of an analyte-containing sample; in contrast to carry-over, it is only the reaction vessels which are immediately physically adjacent in a circular arrangement, and not the positions which follow chronologically/physically, which are affected.

Enzygnost® tests (Dade Behring ELISA System) were to be adapted to the BEP® 2000 System (hardware and software, incl. control software), which was developed by Stratec, Birkenfeld, as machines which were fully automated for ELISA processing.

The BEP® 2000 which is depicted in FIG. 1 is the machine which was developed by Stratec and which is fully automated for, inter alia, processing all the individual steps of an ELISA.

Figure 2:
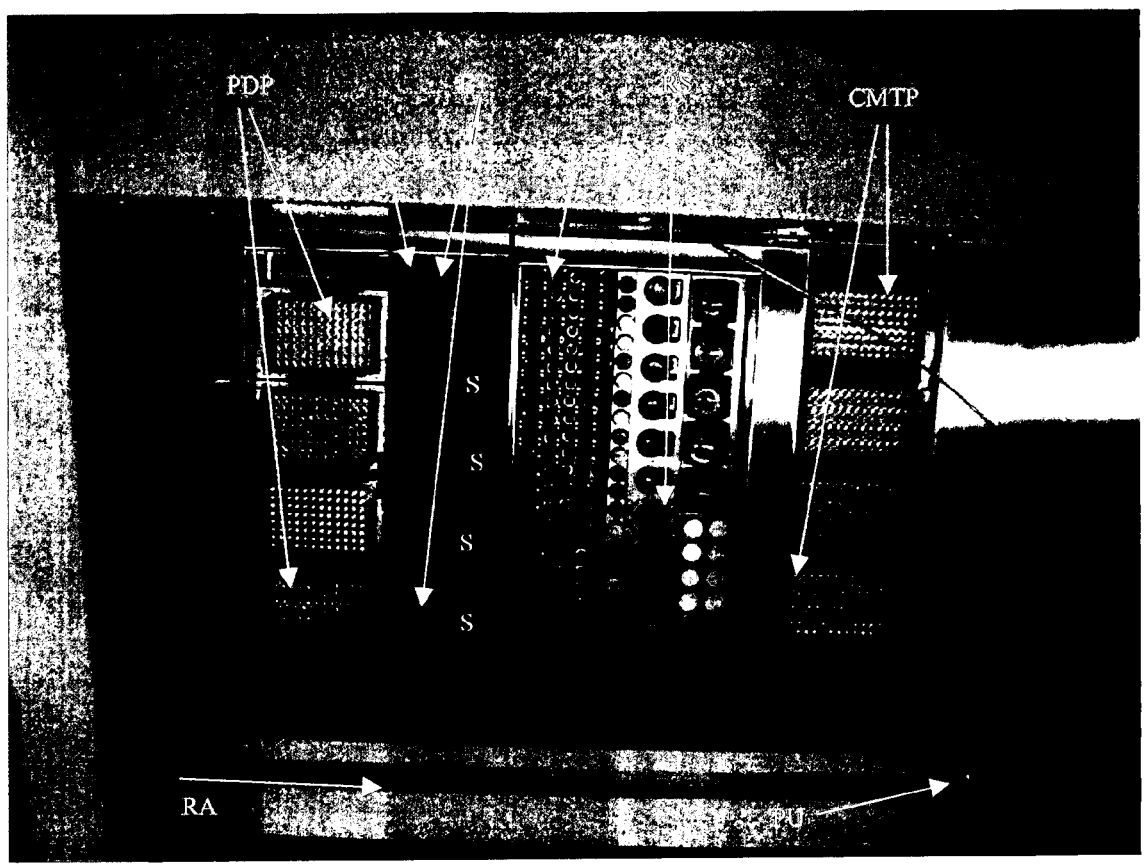

As is evident from FIGS. 1 and 2, the robot arm (RA), which can move on the y plane and which carries the pipettor unit (PU) which can move in the x and z directions, initially picks up a 300 µl or 1 100 µl exchangeable tip (ET) from the store (S) which is provided for them. The RA then approaches the primary tubes (P) and removes a certain aliquot volume of the sample from one tube, with capacitance measurements being used to detect the surface of the liquid and immersion into the sample material only taking place very superficially.

In the case of tests which operate with undiluted sample volumes, the aliquot is pipetted directly into the coated microtitration plates (CMTP) which are presented.

FIG. 3 shows a diagrammatic view down onto the working surface of the BEP 2000 in the region of the coated microtitration plates (from above). The coated plates stand on positions A to D and are loaded with samples, by the pipettor unit, in the sequence A, B, C and D. Subsequently, the liquid waste station (LWS) is approached in order to release sample volume which has been taken up in excess. This excess, also termed "oversoak", is required in order to pipette precisely the sample volume which is effectively required for the test. After the liquid has been released, the discharge position (DP) is approached in order to discharge the disposable tips and to pipette a subsequent sample once again by picking up a new tip.

In the case of tests which operate with previously diluted sample material, the RA moves, before taking up the sample aliquot, over the reagent store (RS) depicted in FIG. 2 in order to initially take up a defined quantity of sample dilution buffer. After the preliminary dilution position (PDP) has been approached, both volumes are delivered into uncoated vessels (microtitration plates or small tubes) and, from there, pipetted into the CMTPs, followed by the sequences as described for undiluted sample processing.

When all the samples, which are defined by way of the software, have been pipetted, in the described sequence, into the CMTPs, which have been provided for the purpose in the positions shown in FIG. 3, the sample material-loaded CMTPs are driven, for the first incubation, into the incubation chambers provided for the purpose using a mechanical transporter (lift). The incubation chambers are located in a working level which is positioned below the sample and/or pipetting level of the instrument and constitute either units whose temperature can be controlled or chambers which are at ambient temperature (room temperature).

The washing device for removing excess sample or reagent liquid from the CMTPs, and the measuring device (photometer or the like) for measuring the test result, are positioned in spatial proximity.

As regards hardware and software, the BEP® 2000 System is, apart from some marginal modifications which do not affect the method according to the invention described below, identical in construction to systems, which have been commercialized under various trade names, and which belong to other suppliers who are marketing the system developed by Stratec under generic names, such as the DiaSorin ETIMax 3000®.

Stratec has optimized both the corresponding hardware configurations and the control software in accordance with the state of the art such that it is not possible to measure one of the above described systematic interferences either by means of pipetting experiments using customary dye solutions or by means of common Enzygnost® test methods.

The Enzygnost® test are ELISA methods for specifically detecting antigens or antibodies in the microtitration plate format, with the underlying test principles being manifold and known to the skilled person.

For example, in the case of conventional antibody determinations, for example rubella-specific antibodies belonging to immunoglobulin class G (IgG), the inner surface of the wells of microtitration plates (reaction vessel or well) is absorptively coated, on the active surface, with the corresponding antigen (in this case: rubella virus antigen).

The user (or the automated machine) predilutes samples to be determined 1:21 in sample buffer and introduces them individually into the wells, where a further dilution of 1:11 takes place (final dilution, 1:231). If specific antibodies are present in the sample material (anti-rubella virus IgG), they then bind to the immobilized antigen (immune complex formation: anti-rubella virus IgG in the sample/rubella virus antigen on the solid phase). After a 1-hour incubation (37° C.), the diluted sample containing excess antibodies is removed by means of repeated washing steps and the solid phase-bound immune complex is incubated with what is termed conjugate (1 h at 37° C.).

The conjugate is anti-human IgG (produced by immunizing rabbits) which has been coupled covalently to horseradish peroxidase (POD) (anti-human IgG/POD conjugate). After this conjugate has been bound to the solid phase-bound immune complex, excess conjugate is removed by means of several washing cycles and incubation then takes place with a chromogen/buffer substrate solution. This is a solution of colorless tetramethylbenzidine, which the POD converts into a blue solution using hydrogen peroxide (substrate).

After a 30-minute incubation at room temperature, the reaction is stopped with stopping solution (sulfuric acid) and the color intensity (extinction) is determined photometrically.

There is a proportional relationship between the color intensity and the concentration of rubella virus-specific antibodies, with the reaction vessels which contain analyte-free samples remaining colorless or giving extinctions which lie below a Cutoff value which is determined for each test by means of clinical trials.

Specific M class antibodies are determined in an analogous manner (for example by means of Enzygnost anti-rubella virus/IgM) using the same solid phase, with the sample dilution only being 1:42 and the conjugate being IgM-specific (anti-human IgM/POD conjugate). Otherwise, the determination takes place as described above.

The following Enzygnost® tests are based on test principles for determining human antigen-specific IgG, with the test principles being structured like Enzygnost® Anti-rubella virus/IgG: Enzygnost®/Anti-CMV/IgG, Anti-EBV/IgG, Anti-HSV/IgG, Anti-VZC/IgG, Anti-measles virus/IgG and Anti-mumps virus/IgG.

When these tests were automatically processed on the BEP® 2000, there was absolutely no contamination of sample material in the form of falsely positive reactions.

However, it was surprisingly observed that, when highly sensitive Enzygnost® tests (for example Anti-HIV and HBsAg) were processed with the BEP® 2000, contaminations nevertheless did occur in an interfering manner.

The difference between the previously mentioned Enzygnost® tests and the highly sensitive Enzygnost® tests which are to be considered here is the following:
  100 µl of undiluted human sample material, and not sample dilutions, are loaded;
  the analytes to be investigated naturally occur in very high concentrations in human serum or plasma.

Enzygnost® HBsAg 5.0 is, for example, an antigen detection method in which the microtitration plate is coated with HBsAG-specific antibody (produced by immunizing sheep).

HBsAg in the sample is simultaneously incubated in the reaction vessels with conjugate 1, which consists of monoclonal HBsAg-specific antibody which is generated in the mouse (one-step method over 60 min at 37° C./antibody sandwich method or immunometric test principle), with the trapping antibody on the solid phase either binding HBsAg/anti-HBsAg antibody complexes or initially binding free HBsAg to which conjugate 1 then attaches in order, then, to bind to the solid phase as an immune complex.

In contrast to the Enzygnost® Anti-rubella virus/IgG and IgM tests which were described at the outset, the marker for the conjugate is not POD but, instead, biotin, which is a vitamin and not an enzyme. The background is a specific amplification system for increasing the sensitivity. In accordance with the state of the art, the exceptionally high affinity of biotin for the protein streptavidin is exploited by incubating with a further conjugate 2 (30 min at 37° C.) after the excess conjugate has been washed out. Conjugate 2 consists of streptavidin to which POD is covalently bonded.

The concluding color development, the stopping of the reaction and the photometric determination, and the evaluation of the extinctions, are effected in analogy with the methodology described for the indirect tests.

The fact that both conjugate 1 and conjugate 2 contain multiple binding partners by way of a carbonate skeleton results, together with the high strength of the binding between biotin and streptavidin, in a dual amplification mechanism, giving a limit for detecting HBsAg which is superior by at least a factor of 5 to that of conventional methods.

Enzygnost® HIV Integral is a method for the combined detection of HIV-specific antibodies (anti-HIV) and HIV antigen (p24 antigen), with both analytes being determined using biotin/streptavidin.

Microtitration plates are coated with immunologically relevant HIV 1, HIV 2 and HIV O proteins, to which antibodies (anti-HIV) which are present in the sample bind in a first incubation (30 min at 37° C.). After excess sample (antibody) has been removed by means of several washing cycles, conjugate 1, which contains HIV antigens (HIV 1, 2 and O) which are bound to a carbonate skeleton at the same time as biotin (antigen sandwich method or immunometric test construction), is then added.

In addition to the HIV proteins, the solid phase contains polyclonal HIV p24-specific antibodies which have been produced by immunizing rabbits. If HIV p24 is present in a sample, it is bound in the above-mentioned incubation and detected with conjugate 1, which additionally contains two monoclonal p24-specific antibodies which have been generated in the mouse and which are bound to carbonate.

After a 30-minute incubation (37° C.) and washing operations, conjugate 2, which, as in the case of Enzygnost® HBsAg 5.0, consists of streptavidin and peroxidase (both components are covalently bonded to a carbonate skeleton), is then added.

The subsequent steps of incubation, washing, chromogen development, stopping and photometric analysis are effected in an identical manner to that described in the case of Enzygnost® HBsAG 5.0.

In the case of this anti-HIV and p24 determination using Enzygnost® HIV Integral, as well, it was possible to demonstrate, within the context of a clinical trial, that it was possible to improve the sensitivity of the test by a factor of more than 4 as compared with previous determination methods.

Both Enzygnost® tests were developed and marketed between 1998 and 1999 in order to take into account the steadily growing demands placed on such tests:

On the one hand, the sensitivity of the HBsAg and HIV determination should be maximal both within the sense of diagnostic reliability and reliability as regards blood donation and, on the other hand, interferences in the sense of falsely positive reactions should be as minimal as possible.

The degree of sensitivity is defined by testing defined sample groups (given in %) by determining samples from very early infection stages (given as the earliest time after infection at which a specific analyte, i.e. antigen or antibody, can first be detected) and by testing serial dilutions of analyte-containing sample material (given in dilution step which was still determined to be positive).

Conversely, the reliability in the case of negative, analyte-free samples is described by way of what is termed the specificity, which indicates, as a percentage, how many negative samples were in fact correctly determined as being negative and, in that case, either after testing once (initial value) or after repeating the samples which were initially reactive (retest value).

Modern HBsAg and anti-HIV determinations which are currently in use exhibit sensitivity values of >99.98%, and typical specificities can be described by >99.3% (initial) and >99.7% (retest). These data are manufacturer-independent, also relate to other analytes such as hepatitis C-specific antibodies (anti-HCV) or Treponema pallidum-specific antibodies (anti-Treponema pallidum) and should, in practice, be achieved independently of the nature of the instrumentation.

Surprisingly, the contaminations which were observed with the BEP® 2000 System affected the specificity characteristic of Enzygnost® HIV Integral and Enzygnost® HBsAg 5.0 such that only initial values of between 92% and 94% were still achieved (see example 3, and also tabs. 1 and 2), even though it was possible by use of the known methods to rule out previously known contaminations, including, in particular, a carry-over effect with regard to the exchangeable tips.

With the aid of model systems which were developed in-house, it was established that the falsely positive reactions were caused by the formation of very small splashes of the order of size of from about 0.1 to 1 nl (corresponds to a dilution of about $1:10^6$) which were formed in connection with the operation of pipetting analyte-containing samples and in connection with the mechanical movement of the pipetting unit.

Furthermore, it was established that less sensitive tests are also affected when, due to the biology, the analyte concerned can occur in extremely high concentrations. Examples of this are the determinations of antibodies directed against hepatitis A virus antigen (anti-HIV) and against hepatitis B virus antigen (anti-HBs).

In addition, models were also used to demonstrate that very small splashes (no visible drops) of the abovementioned order of size, which can lead to interference in high-sensitivity tests, can likewise be formed both when releasing excess sample material and when discharging the exchangeable tips.

In all, therefore, a large number of parameters are affected by interferences which are to be expected independently of the specific configuration of an immunochemical determination method and with any sample dispenser or sample dispenser module which operates in analogy with the BEP® 2000 instrument (such as DiaSorin ETILab®) or is even constructed in the same way as this instrument as regards hardware and system control aspects (for example DiaSorin ETIMax 3000®).

Aside from the ELISA methods which have been described, such effects will prove to be particularly troublesome in connection with applications which are designed for the very highest precision and sensitivity such as recombinant DNA amplification methods in which, as is known, it is possible to measure even the most minor contaminations.

The present invention was now based on the object of systematically describing these new interferences, whose extent was not previously known, and developing methods for ensuring that highly sensitive tests, in particular, are no longer impaired, in the sense of falsely positive findings, or findings which are erroneously too highly positive, as a result of the contamination of sample material.

It has now been found, surprisingly, that it is possible to significantly decrease or prevent the formation of splashes during the pipetting operation by defining a number of characteristic values for the pipettor unit of the BEP® 2000 System.

In addition, it has been found that negative effects which are exerted on the accuracy of the test results by the previously unknown splashes which arise when releasing excess sample volume can be effectively suppressed by installing a mechanical protective device between the liquid waste station and the position for coated microtitration plates.

The invention relates to methods, which are subsequently described in detail, for rapidly visualizing and optimizing the effects and to methods which selectively prevent such contaminations by way of the control software for the pipettor unit. The invention also relates to a hardware amendment or modification of the liquid waste station, with this being possible, for example, in the form of a screen which effectively prevents contaminations in the form of microsplashes.

The present invention consequently relates to a method for reducing the contamination of empty reaction vessels, or reaction vessels which are already charged with analyte-free sample material or sample material which contains analyte at low concentration, within an arrangement of reaction vessels which are located in spatial proximity to each other during the pipetting of samples or reagents using an automatic sample dispenser, which comprises using an enzyme/substrate dye test to initially establish, by means of model A, the extent of the contamination:

a) adding an enzyme solution to reaction vessels in a constituent region of said spatial arrangement while the remaining reaction vessels are covered with an absorbent stratiform material which contains a suitable chromogen/substrate reagent, with a color reaction being induced by its contact with the enzyme, b) determining the number, intensity and/or distribution of the covered reaction vessels which are marked by a color development and subsequently modifying the liquid uptake (aspirate profile) and liquid release (dispense profile) such that the number or intensity of the reaction vessels marked by the color development is reduced.

The invention furthermore relates to a method for reducing the contamination of empty reaction vessels, or reaction vessels which are already charged with analyte-free sample material or sample material which contains analyte at low concentration, within an arrangement of reaction vessels which are located in spatial proximity to each other during the pipetting of samples or reagents using an automatic sample dispenser, which comprises using an enzyme/dye test to initially establish, by means of model B, the extent of the contamination:

a) adding an enzyme solution to reaction vessels in a constituent region of said spatial arrangement,
b) adding a suitable chromogen/substrate reagent, which, on contact with the enzyme, induces a color reaction, to the reaction vessels of the remaining constituent region of said spatial arrangement,
c) ascertaining possible contaminations by determining the color development in the reaction vessels; and subsequently modifying the liquid uptake (aspirate profile) and liquid release (dispense profile) such that the number or intensity of the reaction vessels marked by the color development is reduced.

In said methods according to the invention, the reaction vessels can be wells in a microtitration plate. The present invention relates, in particular, to such a method in which:

a) the automatic sample dispenser is part of a BEP 2000 or of a fully automated machine which is essentially constructed in the same way as the BEP 2000; and
b) the arrangement of reaction vessels which are located in spatial proximity to each other consists of a linear arrangement, which lies in a horizontal plane, of 4 microtitration plates in the sequence: position A, position B, position C and position D as shown in FIG. 3; and
c) a liquid waste station (LWS) is located in immediate proximity to position A in approximate extension of the imaginary line from position D to position A; and
d) the enzyme solution is added to a constituent region of the microtitration plates in positions A to D; and
e) the determination of possible contaminations includes, in particular, the contaminations emanating from the liquid waste station (LWS).

The invention also encompasses a variant of the above-described method in which the liquid waste station (LWS) is covered by an upper covering and an aperture which is present in this covering is made as small as possible such that, on the one hand, optimal protection is provided against splashes from the liquid waste station (LWS) but, on the other hand, it is possible to reproducibly release excess sample volume through this aperture into the liquid waste station (LWS) such that, in connection with this, no liquid inadvertently comes into contact with the edge of the aperture.

The liquid waste station (LWS) can also advantageously be fashioned from the outset such that the upper vessel wall corresponds to the covering, which means that a separate covering can be dispensed with while the function it provides is retained.

It is furthermore advantageous if the liquid waste station (LWS) is separated off by installing a mechanical protective device between the liquid waste station and the positions of the coated microtitration plates, thereby preventing contaminations.

The present invention also relates to a liquid waste station which is suitable for use in one of the above-described methods according to the invention and which is covered by an upper covering, with an aperture which is located in it being as small as possible such that, on the one hand, optimal protection is provided against splashes from the liquid waste station but, on the other hand, it is possible to reproducibly release excess sample volume through this aperture into the liquid waste station such that, in this connection, no liquid inadvertently comes into contact with the edge of the aperture. The liquid waste station can also advantageously be fashioned from the outset such that the upper vessel wall corresponds to the covering, which means that it is possible to dispense with a separate covering while retaining the function which it provides.

Each individual method according to the invention which is described above and each covered liquid waste station according to the invention in itself contributes to avoiding contaminations. Ideally, several or all the methods according to the invention are used, if at all possible in combination with a covered liquid waste station according to the invention, without, however, the present invention being restricted to the combined use.

In accordance with the state of the art, the software for sample dispensers is designed such that it permits the programming of important characteristic values such as the rate of uptake and release of liquids. This is even regarded as being essential since these features have to be adapted to the properties (such as viscosity) of the material being investigated (A. Frittrang; Laborpraxis [Laboratory practice], December 1996). However, these adaptations, like optimizations of the precision syringes (what are termed dilutors) or of the needle diameters, are generally only undertaken in connection with optimizing the precision and accuracy of the pipetting volume. The programming itself can be implemented by way of firmware modules or control software belonging to the overall system and even be available to the user as a component of the operational software.

Further examples from the literature which may be mentioned are the directions provided by the company Tecan on the topic of liquid handling: Liquid Handling Manual for DITI 200 AC/C (Docu. No. 390548); Option DITI 200 AC/C (Docu. No. 390542); Gemini Software manual No. 39 1354 V3.10 dated September 1999 (manual No. 391354, V 3.10). In these manuals, as well as in relevant textbooks, such as W. Wagner: "Strömungstechnik und Druckverlust-Berechnung" [Flow Technology and Pressure Loss Calculation]; Vogel Buchverlag, changes in the uptake and release parameters are described in connection with the precision and accuracy of the pipetting processes while paying particular attention to the viscosity of a given sample material. However, there are no specific directions for detecting or avoiding contaminations by very small sample volumes either in the optimization instructions in this regard or in corresponding lists of possible sources of error (what are termed trouble-shooting guides).

The only direction in the Liquid Handling Manual for DITI 200 AC/C (see above) relates to pronounced, visually discernible drop formation at the outlet of the tips and thereby describes, if anything, a technical fault or incorrectly programmed function rather than a selective measure for avoiding very small splashes ("microsplashes") in the nanoliter scale.

As is the case with most pipetting robots, it is also possible, in the case of BEP 2000, to change software settings in what is termed the "System Setup" in order to change the physical characteristic values for sample uptake and release.

Examples of such settings which were selectively modified within the meaning of the present invention in the case of sample uptake (aspirate profile, see FIG. 5) are:
"Start velocity" describes the initial velocity of sample uptake;
"Top velocity" describes the maximum velocity of sample uptake achieved;
"Dive out velocity" describes the velocity with which the tip is moved out of the liquid following sample uptake.

Examples of such settings which were selectively modified within the meaning of the present invention in the case of sample release ("dispense profile", see FIG. 5) are:
"Start velocity" describes the initial velocity of sample release;
"Top velocity" describes the maximum velocity of sample release achieved;
"Acceleration" describes the acceleration of sample release;
"Cutoff velocity" describes the acceleration velocity when sample release is terminated (cutout velocity when the operation is terminated);
"Dive out velocity" describes the velocity with which the tip is moved away from the position above the reaction vessels following sample release.

The company Stratec optimized all the above-mentioned parameters in accordance with the state of the art, while taking into consideration the contamination effects described at the outset, such that the appropriate criteria were met. The final arrangement which Stratec worked out on this basis corresponds to the settings shown in FIG. 5.

These profile settings shown in FIG. 5 were tested on the automatic processing of, for example, the test systems Enzygost® Anti-HBc monoclonal, Enzygnost® Anti-HBc/IgM, Enzygnost® Anti-HAV/IgM, Enzygnost® HBeAg monoclonal, Enzygnost® Anti-CMV/IgG+IgM, Enzygnost® Anti-CMV/IgG, Enzygnost® Anti-CMV/IgM, Enzygnost® Anti-rubella virus/IgG, Enzygnost® Anti-rubella virus/IgM, Enzygnost® Anti-HSV/IgG, Enzygnost® Anti-HSV/IgM, Enzygnost® Toxoplasmosis/IgG, Enzygnost® Toxoplas-mosis/IgM, Enzygnost® Borreliosis/IgG and Enzygnost® Borreliosis/IgM, and excellent agreement was achieved for all the human samples which were negative or positive in accordance with the immune status.

For the test, 16 reactive samples (A1 to H2, see also FIG. 4) and more than 30 human samples which were negative as regards the respective analyte were loaded simultaneously onto a microtitration plate and examined in the abovementioned tests.

The measurement results (extinction units) for toxoplasmosis IgG, rubella IgG and HSV IgG, which are shown, by way of example, in tabs. 3, 4 and 5, make it clear that absolutely no indication of any contaminations, in whatever way they might have come about, can be detected in these methods, even in connection with the mixed loading of samples: samples containing extremely high concentrations of the analyte to be investigated, on the one hand, and analyte-free samples, on the other hand, were loaded onto the same test plate.

However, a significant interference due to cross contaminations of sample material was surprisingly detected with the pipettor profile shown in FIG. 5 (state of the art) when carrying out mixed pipetting of analyte-containing and analyte-free samples in connection with using Enzygnost® HBsAg 5.0 and Enzygnost® HIV Integral. The processing took place in the A position of the primary locations of the coated microtitration plates (in this regard, see also FIG. 3).

As the measurement results (of the anti-HIV and HBsAg determination) shown in tables 1 and 2 make clear, there are on average from 4 to 6 falsely positive individual results per test plate (e.g. at microtitration plate positions A1, F5, F7 and A8 in tab. 1). Based on on the total number of approx. 60 analyte-free samples, this effect results in specificity data of between 92 and 94% whereas the manual loading of samples, which was carried out in parallel, together with subsequent processing using the BEP III® (Dade Behring automated ELISA processor) did not produce any falsely positive values.

The model A described in example 1 was developed for optimizing the release settings for the BEP® 2000 pipettor. This model A is an extremely sensitive enzyme/dye test in which 100 µl of a highly concentrated enzyme solution (0.25 mg of peroxidase/ml) are loaded by the pipettor into rows 5 to 8 of an empty, uncoated microtitration plate (see also FIG. 4 in this regard). The corresponding rows 1 to 4 and 9 to 12 were covered with filter paper (which was supported by a solid plastic carrier) which was soaked with chromogen/buffer substrate solution. The working solution was prepared in accordance with the pack enclosure and is described in example 1.

In order to make the matrix more comparable (for example in the interest of the applicability of the results as regards viscosity properties), serum from healthy blood donors was chosen as the dilution medium.

Figure 6:
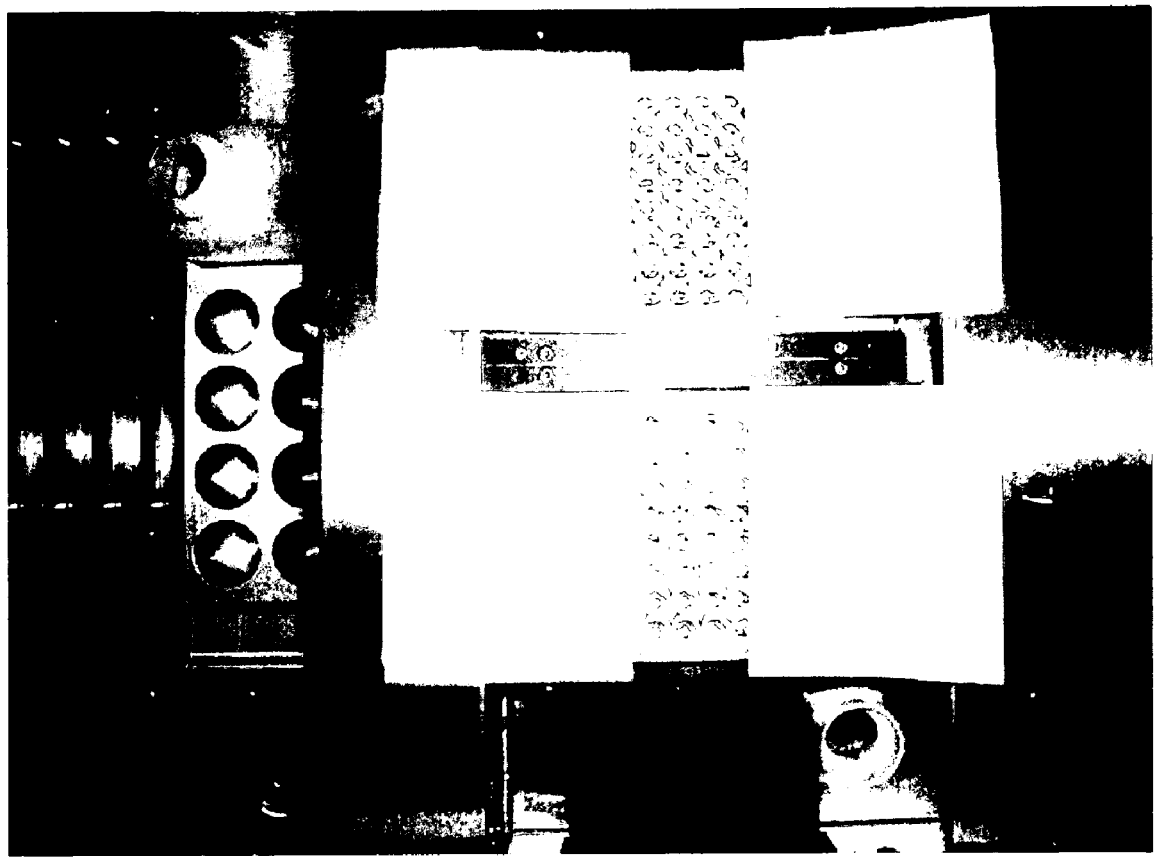

It was surprisingly found, when using this simple model, that very many splashes of a very wide variety of sizes occur (FIG. 6).

The quantification of the reliable detection limit of this method gave a value of about 0.25 ng of POD/ml, which corresponds to a dilution of somewhat greater than $1:10^5$ or to a droplet formation of the order of size of 1.0 nl. It is consequently possible to use this method to visualize contaminations which lie beyond the limit which is discernible visually as drops but which nevertheless interfere in highly sensitive detection methods.

Figure 8:
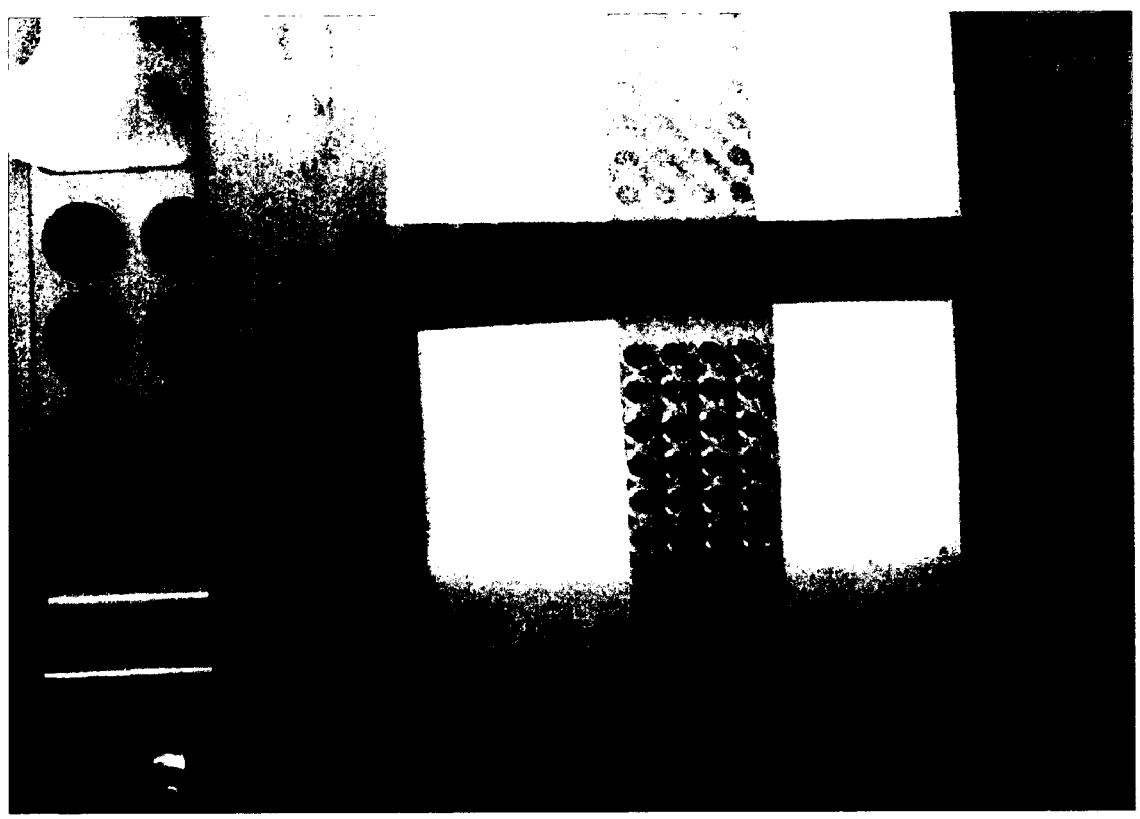

The optimizations which were carried out using this model (model A) led to the arrangements of the dispense profile which are summarized in FIG. 7 and to the improvements which were detected and are shown in FIG. 8.

While success was also achieved in producing contaminations which were minimized by the measures using Enzygnost® HBsAg 5.0, it was not possible to eliminate them completely.

On the assumption that, while aerosols which arise during the pipetting operation constitute one cause, other influence quantities are also active, another system, i.e. model B (see example 2), was developed, which system was intended to enable very small splashes to be assigned more clearly to the site of origin.

For this, 100 µl of the concentrated POD solution were loaded into rows 1–4 on a microtitration plate in the C position using the BEP® 2000 instrument (in this regard, see also FIG. 3 and FIG. 4), while the chromogen/buffer substrate solution was loaded into rows 5 to 12. All the strips in the plates in positions B and A were loaded only with chromogen/buffer substrate solution; after 30 mm, the reactions were stopped and the extinctions were measured photometrically at all positions.

Quantification of the reliable detection limit for this method gave a value of 25 pg of POD/ml, which corresponds to a dilution of about $1:10^7$ or to a droplet formation in the order of size of 0.01 nl.

Model B thereby proves to be substantially more sensitive than model A and permits highly sensitive detection of contaminations beyond the sensitivity limits known from the state of the art (see example 2).

The surprising result under standard profile settings (in accordance with the state of the art) was that the plates in the B position and in the A position, in addition to the plate in the C position, were strongly affected by contaminations (tabs. 6, 7 and 8). Whereas the C position can be explained, using model A, as "aerosols" due to the shunting operation, other influence quantities must be active for the contamination of plates in B and A since it cannot be assumed that the splashes are propelled over such large distances.

All the variables of the aspiration (aspirate) and release (dispense) functions were experimentally varied individually and the consequences resulting from this were tested in model A or model B (or in both). Use was made of an iterative procedure in which each of the variables described on pages 18 and 19 were systematically optimized in regard to the contamination effects. Successful model results were verified by using the BEP® 2000 to automatically process the described Enzygnost® tests.

Using model B while having optimized the profile settings for the dispensing function (FIG. 7) confirmed this assumption: the marked decrease in contaminations in C but still cross contaminations in A and B (tabs. 9, 10 and 11).

The possibility of the outside of the tips being wetted and this causing liquid to drop off when the pipettor was moved over the microtitration plates seemed improbable since the exchangeable tips detect the surface of the liquid by way of a capacitive measurement system and, as a consequence, only dip into the sample liquid to a slight extent for the purpose of sampling.

Entirely unexpectedly, the use of model B demonstrated the effect of the loss of very small sample volumes (of the order of size of between 0.01 and 0.5 nl) during the operation of transporting the BEP 2000 pipetting unit; this can be effectively suppressed by using suitable profiles in the aspiration phase (aspirate profile in FIG. 9), as the reduced effects of contamination in model B on plate position B, as seen in tab. 12, make clear.

When used with model B, the optimized aspirate profiles, together with the optimized dispense profiles (FIGS. 7 and 9), produce the typical improvements in the contamination effects which are shown in tabs. 13 to 15. However, it is also clear from these tables that contaminations still occur at plate position A, with these contaminations clustering in the lower rows (tab. 13).

When an attempt was made to cover the liquid waste station (position LWS in FIG. 3) while at the same time using optimized aspirate and dispense profiles, it was surprisingly found that this resulted in the plates in positions A, B and C being absolutely clean.

This makes it certain that additional splashes can arise when sample volumes which have been taken up in excess (oversoak) are released into the waste station, with these splashes giving rise to the staining which was observed. Since the oversoak is indispensable for ensuring reliable and precise pipetting of the samples into the reaction vessels, a cover was developed as depicted in FIG. 10.

The contaminations in plate position A, which were described at the outset and which were observed with the standard profile settings and Enzygnost® HBsAg, can in summary, using the descriptions from model B, be attributed to three different splash sources which can be described, and remedied (measures in brackets), separately from each other both as regards location and as regards cause:

splashes due to the operation of pipetting samples (optimizing the dispense profiles);

splashes due to tailing/dripping effects associated with the pipettor (optimizing the aspirate profiles), and splashes due to release of excess sample volume (mechanically screening off the liquid waste station, for example by means of a covering).

Figure 11:
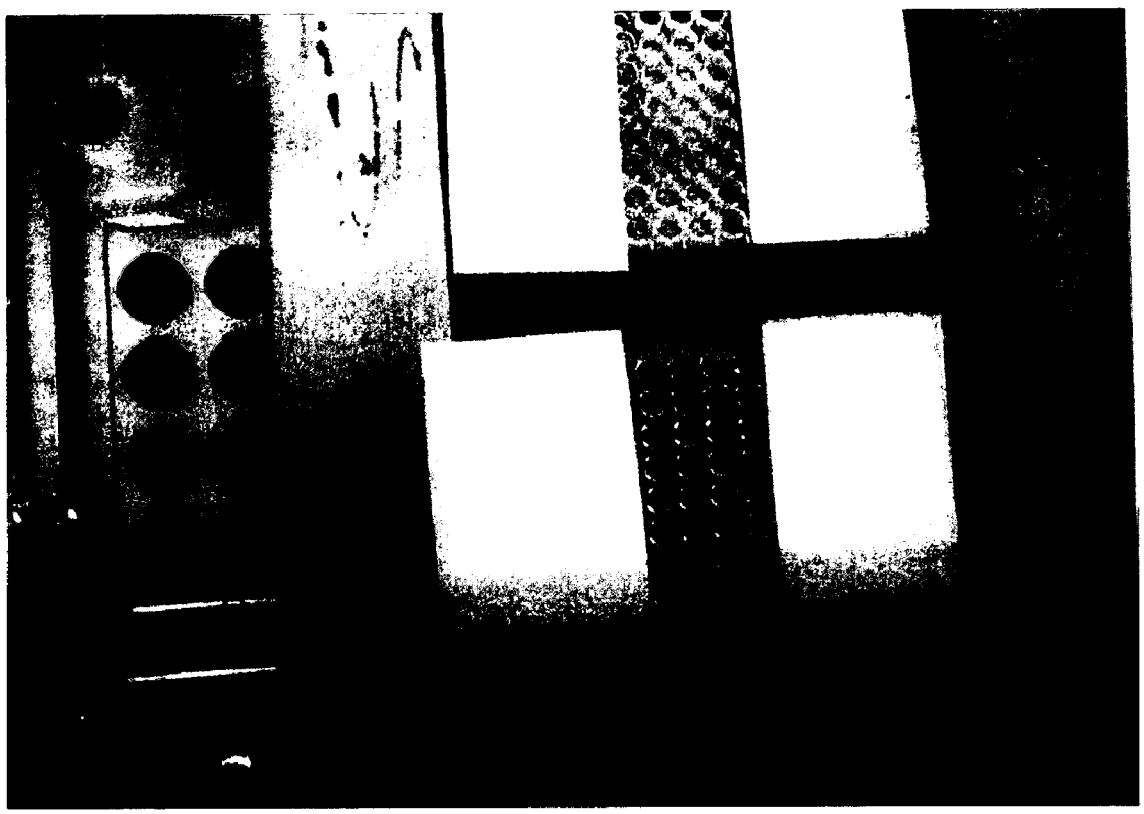

It can be shown that each measure individually contributes to improving the contamination effects. However, the effects are only completely reduced when all the measures are implemented, giving the resulting image in model A as shown in FIG. 11.

The efficiency of the described measures can be verified, with corresponding results as well, when using Enzygnost® HBsAg 5.0 (tab. 16) and Enzygnost® HIV Integral (tab. 17), with the plates in the tables being tested at position A.

The colorations which are visible in strip 4 in the microtitration plate shown in tab. 18 are an expression of the initially described spill-over effects, which may occur very rarely. When the application of model B to ELISA methods, as described in example 3, was carried out, by taking random samples, on the Tecan RSP 150% (with subsequent automated processing of the Enzygnost® HBsAG 5.0 using the Dade Behring BEP® III), it was shown that this sample dispenser can display the same effect as the BEP® 2000 prior to implementing the observations which were surprisingly made (tab. 19).

In addition to this, the results which were obtained under the same conditions using Enzygnost® HBsAg 5.0, as shown in tab. 20, make it clear that this pipetting robot can measure contaminations, however they may be produced, as being interfering, something which no longer occurs in the case of the BEP 2000 after the method according to the invention has been implemented.

It was thus surprisingly also possible to show that the sensitivity of individual diagnostic detection methods has very recently increased such that contamination effects which are caused by pipetting robots or sample dispenser modules, and which were previously tolerable, can cause troublesome, if not actually misleading, erroneous interpretations when using present-day highly sensitive detection methods.

Over and above the two Enzygnost® tests, contaminations were also observed in the case of less sensitive determination methods, i.e. Enzygnost® Anti-HBs, Anti-HIV (total Ig) and Anti-HBe (tabs 21, 22 and 23), with, however, these contaminations being less noticeable both as regards frequency and as regards distinctiveness. Since, in this case, these are parameters in connection with which the skilled person knows that very high analyte concentrations can occur naturally, this suggests that, in this case, the limits in accordance with the state of the art are no longer sufficient for ensuring a reliable, contamination-free determination. In the case of these tests, too, it can be shown that the effects can be brought under control when all the described measures are used.

Finally, a previously undescribed cause of contaminations in the liquid waste station (LWS) is identified, which, as an additional source of error, can produce erroneous results which can, however, be rapidly and reliably prevented mechanically, for example by installing a suitable lid which has an aperture, for inserting excess sample volumes (liquid waste), located in it.

Accordingly, the invention relates to a method in which the liquid waste station (LWS) is covered by an upper covering, and an aperture, which is present in the covering, is as small as possible such that, on the one hand, optimal protection against splashes from the liquid waste station (LWS) is provided but, on the other hand, excess sample volume can be released reproducibly through this aperture into the liquid waste station (LWS) such that no liquid inadvertently comes into contact with the edge of the aperture.

Alternatively, the liquid waste station (LWS) can from the outset be fashioned such that the upper vessel wall corresponds to the abovementioned covering such that a separate covering can be dispensed with while retaining the function it provides.

Instead of, or in addition to, the above-described covering or corresponding configuration of the liquid waste station without covering, it is also possible to install a separating device, for example a separating wall, between the liquid waste station and the region of the reaction vessels (for example microtitration plates).

The measures taken, according to the invention, to optimize the profiles, and the mechanical amendment to the hardware, are derived using one particular embodiment of a sample dispensing station and are consequently directly and immediately applicable to appliances which are constructed in the same manner.

In the case of instruments which are designed in an analogous manner, the skilled person can make use of these methods even if the programmings which are required in this regard have to be performed in a different manner. Thus, it is to be expected that other characteristic value names exist, other measurement units define the settings and/or that the programming is, or has to be, performed in other software hierarchies (for example Firmware, control software or even directly in the structure of the operating system of the software in dedicated PCs and/or software structures intrinsic to the system). In all cases, the method according to the invention retains its applicability and can be used in analogous adaptations, which are obvious to the skilled person, to a given system.

In particular, a skilled person can also use the methods, which, as models A and B, permit a rapid inventory and, in particular, optimization of existing contaminations, in their entirety, for appropriate conversions and modifications, on 4-channel or 8-channel pipettors which are equipped either with stainless steel needles or with exchangeable tips.

The lid, which is described as a covering of the liquid waste station, can be modified, for example either by designing and constructing it as an overall solution to the liquid waste station (in the form of a component), or designing it differently geometrically/physically, or implementing it entirely differently, within the meaning of the method according to the invention, for example by installing a separating wall between the liquid waste station and the CMTPs, or other constructions, for screening off and thereby preventing the contaminations.

It is likewise possible, armed with the knowledge that areas which were previously not given sufficient consideration (for example the liquid waste station) have substantial potential for interference, to draw conclusions with regard to other potential sources of interference (such as the pipetting discharge station).

The present invention is also explained below by the examples and the patent claims without, however, being restricted to any of the specific embodiments which are mentioned.

EXAMPLE 1

Model A for Detecting Contaminations from Sample Dispensers

POD Stock Solution:
Horseradish peroxidase (POD) is dissolved, at a concentration of 0.25 mg/ml, in normal serum derived from a healthy blood donor in order to produce a matrix for pipetting which is comparable to the natural sample material as regards viscosity and other physico-chemical properties.

Chromogen/Buffer Substrate Solution:
This is a product marketed by Dade Behring: "supplementary Reagents for Enzygnost®/TMB", (Code # OUVP G17).
Soln. 1 Chromogen TMB:
5 g of tetramethylbenzidine/L of water;
Soln. 2 Buffer/TMB substrate:
approx. 0.1 g of hydrogen peroxide/L of sodium acetate buffer.
1 ml of chromogen TMB is mixed with 10 ml of buffer/TMB substrate in a plastic bottle which is contained in a test kit. This working solution can be used for up to 5 days when stored in the dark at from +2 to +8° C.

Tips:
Conductive 300 µl and 1 100 µl exchangeable tips (from Eppendorff).

Implementing Model A:
Pieces of a size of approx. 5×8 cm are cut from a plastic film (in this case: adhesive films for microtitration plates from the abovementioned test kit) and absorbent paper (for example Schleicher & Schüll) which has been cut to the same size is laid on them. The paper is then soaked with approx. 2 ml of the chromogen/buffer substrate working solution.

In each case, 2 papers which have been prepared in this way are used, on plastic supports, for covering strips 1 to 4 or 9 to 12 (see also FIG. 4) of an uncoated microtitration plate.

The BEP® 2000 pipetting robot is now used to pipette in each case 100 µl of the POD stock solution into the open strips 5 to 8 and the result is documented by photographing the papers after 10 min.

Contaminations which take place appear as blue punctate stains whose diameter and color intensity are directly proportional to the extent of the contaminations.

By means of carrying out serial dilutions of the POD stock solution and applying defined volumes of the dilution steps to chromogen/buffer substrate-soaked absorbent papers, it was possible to use the 10-minute incubation to determine a detection limit of less than 2.5 ng of POD/ml, which corresponds to a dilution of $1:10^5$ (and greater).

EXAMPLE 2

Model B for Detecting Contaminations

Materials:
The solutions and tips used were, without exception, those described in example 1, while, in order to increase the detection sensitivity, a time of 30 min was laid down for developing the chromogen in this model. In addition, the model requires the stock solution (0.5 N sulfuric acid), which is used to stop the dye formation after the 30-minute incubation in order to quantify the color intensity using a photometer (measurement at 450 nm measurement wavelength and 650 nm reference wavelength within one hour after stopping).

Implementing Model B:

3 uncoated microtitration plates are placed on positions A, B and C as defined in FIG. 3.

All the wells in the plates in the A and B positions are firstly filled completely with in each case 100 µl 0.30 of the chromogen/buffer substrate working solution, as are strips 5 to 12 in the plate in the C position (in this regard, see FIG. 3).

The pipetting robot then pipettes 100 µl of the concentrated POD solution only into strips 1 to 4 in the plate in the C position, and all the plates are driven into the room temperature chambers of the BEP® 2000. After 30 min, the reaction is stopped by adding 100 µl of stopping solution and the extinction in each reaction vessel (well) in each plate is determined photometrically.

Contaminations which take place appear as yellow discolorations in individual wells of the affected microtitration plates, the color intensities of which discolorations are directly proportional to the severity of the contaminations. Exemplary results are depicted in tabs. 6, 7 and 8.

The detection limit for the method was determined by pipetting in each case 10 µl of defined serial dilutions of the POD stock solution into in each case 100 µl of the chromogen/buffer substrate solution.

The extinctions of the individual concentrations, which were measured photometrically after stopping the reaction, are summarized in the following table in comparison with background values and lead to a sensitivity limit of less than 25 pg of POD/ml, corresponding to a dilution of $1:10^7$.

TABLE 24

Extinctions of different POD concentrations in model B

| Concentration: ng of POD/ml | Extinction at 450 nm (OD) | Corresponding to a dilution of the stock solution of |
|---|---|---|
| 2.5 | Overflow | $10^5$ |
| 0.25 | 1.780 | $10^6$ |
| 0.025 | 0.180 | $10^7$ |
| 0.0025 | 0.080 | $10^8$ |
| Background (mean value from n= 20 individual measurements) | 0.020 | Negative |

Variations of Model B:

In one of these, 3 plates are not positioned; instead, only one single plate is positioned in the A position, with its loading/pipetting scheme corresponding to that of plate C in model B. The plate is processed entirely as described above.

Depending on the problem, it is also possible to investigate 4 plates on all the plate positions while varying the sites at which the enzyme solution is loaded very widely.

EXAMPLE 3

Application of Model B to Enzygnost® Tests

In this case, approx. 20–30 sera containing high concentrations of the analyte to be determined are loaded into the first 3 strips and approx. 70 analyte-free sera are loaded into the remaining wells in the microtitration plates for the Enzygnost® tests.

The plate is positioned either at position A (variation of model B) or at position C when microtitration plates which are exclusively loaded with analyte-free sera are additionally placed on positions A and B.

The BEP® 2000 carries out the further processing of the plates, in a fully automated manner and depending on the test, in accordance with the methods which are described in the corresponding pack enclosures for the Enzygnost® tests.

In addition, comparison tests using the identical plate loadings are performed, with the samples being pipetted manually and the ELISA being carried out in parallel using the BEP III®. This makes it possible to identify samples which naturally (matrix-associated) generate higher OD values which cannot be attributed to contaminations.

Exemplary results obtained from applying the loading scheme to Enzygnost® tests are recorded, in the case of HBsAG, in tab. 1 (before applying the methods according to the invention) and tab. 16 (after implementing the inventions).

TABLE 1

Enzygnost HIV Integral
Testing of 30 pos. samples in positions E1-B5, 58 neg. samples in positions C5-D12 Negative control in positions A1-C1 and positive control in positions D1 and E12-H12
Cutoff = 500 mE (0.5 OD)

| | Strips: | | | | | | | | | | | |
|---|---|---|---|---|---|---|---|---|---|---|---|---|
| Row: | 1 | 2 | 3 | 4 | 5 | 6 | 7 | 8 | 9 | 10 | 11 | 12 |
| A | 751 | 3000 | 3000 | 3000 | 3000 | 28 | 130 | 3000 | 31 | 29 | 62 | 26 |
| B | 49 | 3000 | 3000 | 3000 | 3000 | 46 | 33 | 39 | 41 | 25 | 40 | 27 |
| C | 269 | 3000 | 3000 | 3000 | 47 | 40 | 42 | 32 | 33 | 37 | 33 | 28 |
| D | 1485 | 3000 | 3000 | 3000 | 46 | 36 | 29 | 31 | 31 | 28 | 25 | 44 |
| E | 3000 | 3000 | 3000 | 3000 | 33 | 60 | 41 | 41 | 48 | 185 | 25 | 1045 |
| F | 3000 | 3000 | 3000 | 3000 | 1366 | 222 | 1164 | 34 | 32 | 38 | 27 | 988 |
| G | 3000 | 3000 | 3000 | 3000 | 33 | 103 | 157 | 40 | 37 | 33 | 30 | 1078 |
| H | 3000 | 3000 | 3000 | 3000 | 37 | 36 | 93 | 31 | 30 | 59 | 40 | 993 |

Values represent extinctions in mE, as were measured at the measurement wavelength of 450

TABLE 2

Enzygnost HBsAg 5.0
Testing of 20 pos. samples in positions E1-H3, 71 neg. samples in positions A4-G12 Negative control in positions A1-C1 and positive control in positions D1 and H12
Cutoff = 85 mE, corresponding to = 0.085 OD Strips:

| Row: | 1 | 2 | 3 | 4 | 5 | 6 | 7 | 8 | 9 | 10 | 11 | 12 |
|---|---|---|---|---|---|---|---|---|---|---|---|---|
| A | 33 | 3000 | 3000 | 20 | 24 | 24 | 16 | 19 | 19 | 26 | 23 | 24 |
| B | 34 | 3000 | 3000 | 15 | 20 | 15 | 51 | 21 | 17 | 22 | 26 | 26 |
| C | 38 | 3000 | 3000 | 77 | 22 | 14 | 16 | 13 | 17 | 17 | 3000 | 26 |
| D | 1802 | 3000 | 3000 | 20 | 21 | 17 | 15 | 21 | 15 | 44 | 24 | 40 |
| E | 3000 | 3000 | 3000 | 18 | 17 | 24 | 16 | 24 | 268 | 21 | 22 | 58 |
| F | 3000 | 3000 | 3000 | 21 | 18 | 21 | 18 | 20 | 19 | 18 | 21 | 41 |
| G | 3000 | 3000 | 3000 | 50 | 16 | 720 | 21 | 17 | 27 | 25 | 21 | 26 |
| H | 3000 | 3000 | 3000 | 13 | 17 | 17 | 21 | 258 | 207 | 3000 | 20 | 1565 |

Values represent extinctions in mE, as were measured at the measurement wavelength of 450

TABLE 3

Enzygnost Toxoplasmosis IgG
Testing of 21 pos. samples in positions D1-H3, 71 neg. samples in positions A4-G12 Negative control in positions A1-B1 and positive control in positions C1 and H12
Cutoff = 100 mE, corresponding to = 0.1 OD Strips:

| Row: | 1 | 2 | 3 | 4 | 5 | 6 | 7 | 8 | 9 | 10 | 11 | 12 |
|---|---|---|---|---|---|---|---|---|---|---|---|---|
| A | 20 | 1515 | 2225 | 70 | 27 | 67 | 35 | 57 | 29 | 67 | 41 | 25 |
| B | 27 | 1977 | 1393 | 23 | 35 | 54 | 44 | 28 | 51 | 44 | 35 | 53 |
| C | 1603 | 1719 | 2514 | 31 | 43 | 27 | 36 | 31 | 30 | 39 | 29 | 33 |
| D | 2119 | 2389 | 1925 | 50 | 69 | 31 | 42 | 65 | 49 | 59 | 28 | 47 |
| E | 1629 | 2292 | 1865 | 27 | 29 | 49 | 51 | 26 | 53 | 29 | 52 | 38 |
| F | 1266 | 2112 | 1896 | 35 | 46 | 45 | 43 | 46 | 57 | 36 | 48 | 62 |
| G | 1958 | 2367 | 1476 | 28 | 58 | 28 | 54 | 39 | 32 | 33 | 43 | 28 |
| H | 2091 | 2115 | 1993 | 40 | 53 | 25 | 56 | 70 | 29 | 41 | 41 | 1753 |

Values represent extinctions in mE, as were measured at the measurement wavelength of 450

TABLE 4

Enzygnost Anti-rubella virus/IgG
Testing of 15 pos. samples in positions B1-H4, 31 neg. samples in positions A5-G12
Positive control in positions A1/A2 and H11/H12
Cutoff = 100 mE, corresponding to = 0.1 OD Strips:

| Row: | 1 | 2 | 3 | 4 | 5 | 6 | 7 | 8 | 9 | 10 | 11 | 12 |
|---|---|---|---|---|---|---|---|---|---|---|---|---|
| A |  | 1355 |  | 1440 |  | 4 |  | 2 |  | 1 |  | 5 |
| B |  | 2629 |  | 1129 |  | 2 |  | 4 |  | 9 |  | 12 |
| C |  | 2322 |  | 2189 |  | 5 |  | 11 |  | 5 |  | 9 |
| D |  | 1910 |  | 1426 |  | 2 |  | 3 |  | 7 |  | 4 |
| E |  | 1470 |  | 1443 |  | 10 |  | 2 |  | 8 |  | 10 |
| F |  | 1197 |  | 2032 |  | 5 |  | 1 |  | 5 |  | 3 |
| G |  | 953 |  | 1743 |  | 6 |  | 5 |  | 4 |  | 1 |
| H |  | 646 |  | 1977 |  | 5 |  | 4 |  | 3 |  | 1223 |

Values represent extinction differences in mE, between a specific signal (antigen coating in rows 1, 3, 5, 7, 9 and 11) and a nonspecific signal (control antigen in rows 2, 4, 6, 8, 10 and 12).

TABLE 5

Enzygnost Anti-HSV/IgG
Testing of 15 pos. samples in positions B1-H4, 31 neg. samples in positions A5-G12
Positive control in positions A1/A2 and H11/H12
Cutoff = 100 mE, corresponding to = 0.1 OD Strips:

| Row: | 1 | 2 | 3 | 4 | 5 | 6 | 7 | 8 | 9 | 10 | 11 | 12 |
|---|---|---|---|---|---|---|---|---|---|---|---|---|
| A |  | 1541 |  | 1440 |  | 50 |  | 24 |  | 32 |  | 32 |
| B |  | 2239 |  | 1359 |  | 45 |  | 11 |  | 33 |  | 19 |
| C |  | 1833 |  | 782 |  | 40 |  | 26 |  | 26 |  | 23 |
| D |  | 1791 |  | 1921 |  | 46 |  | 33 |  | 27 |  | 31 |
| E |  | 1089 |  | 1533 |  | 49 |  | 41 |  | 33 |  | 36 |
| F |  | 1204 |  | 1171 |  | 33 |  | 39 |  | 19 |  | 29 |
| G |  | 1089 |  | 1714 |  | 29 |  | 35 |  | 28 |  | 35 |
| H |  | 1791 |  | 1519 |  | 42 |  | 28 |  | 17 |  | 1405 |

Values represent extinction differences in mE, between a specific signal (antigen coating in rows 1, 3, 5, 7, 9 and 11) and a nonspecific signal (control antigen in rows 2, 4, 6, 8, 10 and 12).

TABLE 6

Model B in accordance with example 2
The plate was located in position C as shown in FIG. 3

Strips:

| Row: | 1 | 2 | 3 | 4 | 5 | 6 | 7 | 8 | 9 | 10 | 11 | 12 |
|---|---|---|---|---|---|---|---|---|---|---|---|---|
| A | 96 | 96 | 93 | 96 | 10 | 10 | 10 | 10 | 10 | 10 | 10 | 11 |
| B | 97 | 96 | 96 | 98 | 10 | 10 | 10 | 9 | 10 | 10 | 10 | 10 |
| C | 98 | 98 | 96 | 97 | 10 | 10 | 10 | 10 | 10 | 10 | 10 | 10 |
| D | 94 | 97 | 94 | 109 | 10 | 10 | 10 | 11 | 10 | 10 | 10 | 10 |
| E | 93 | 93 | 103 | 93 | 9 | 37 | 17 | 12 | 10 | 10 | 10 | 10 |
| F | 95 | 98 | 98 | 97 | 10 | 266 | 19 | 10 | 10 | 10 | 9 | 9 |
| G | 98 | 95 | 99 | 98 | 10 | 309 | 11 | 10 | 10 | 10 | 10 | 10 |
| H | 94 | 99 | 95 | 97 | 1389 | 2039 | 11 | 11 | 10 | 11 | 11 | 11 |

Values represent extinctions in mE, as were measured at the measurement wavelength of 450

TABLE 7

Model B in accordance with example 2
The plate was located in position B as shown in FIG. 3

| Row: | Strips: | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 15 | 15 | 2886 | 15 | 14 | 1005 | 14 | 15 | 15 | 17 | 15 | 15 |
| B | 15 | 15 | 15 | 15 | 1179 | 15 | 18 | 2763 | 14 | 14 | 14 | 15 |
| C | 15 | 15 | 15 | 17 | 14 | 1782 | 15 | 15 | 15 | 3000 | 15 | 15 |
| D | 15 | 14 | 14 | 15 | 14 | 14 | 14 | 14 | 15 | 14 | 14 | 13 |
| E | 14 | 14 | 14 | 15 | 18 | 14 | 14 | 13 | 18 | 14 | 14 | 16 |
| F | 15 | 14 | 15 | 14 | 21 | 15 | 14 | 14 | 17 | 16 | 16 | 16 |
| G | 15 | 15 | 14 | 14 | 3000 | 15 | 15 | 18 | 17 | 17 | 14 | 17 |
| H | 16 | 15 | 15 | 15 | 20 | 15 | 15 | 14 | 17 | 18 | 14 | 17 |

Values represent extinctions in mE, as were measured at the measurement wavelength of 450

TABLE 8

Model B in accordance with example 2
The plate was located in position A as shown in FIG. 3

| Row: | Strips: | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 14 | 13 | 14 | 14 | 14 | 13 | 15 | 15 | 14 | 13 | 13 | 14 |
| B | 15 | 14 | 15 | 14 | 15 | 15 | 13 | 15 | 14 | 14 | 14 | 34 |
| C | 15 | 14 | 14 | 14 | 14 | 14 | 13 | 14 | 14 | 14 | 14 | 14 |
| D | 13 | 13 | 14 | 15 | 14 | 28 | 13 | 13 | 30 | 13 | 12 | 36 |
| E | 13 | 14 | 14 | 13 | 14 | 14 | 19 | 14 | 14 | 17 | 125 | 14 |
| F | 14 | 13 | 13 | 13 | 13 | 33 | 33 | 23 | 18 | 18 | 535 | 19 |
| G | 14 | 14 | 14 | 13 | 13 | 22 | 13 | 30 | 18 | 17 | 547 | 23 |
| H | 15 | 14 | 19 | 14 | 13 | 14 | 27 | 38 | 37 | 35 | 343 | 21 |

Values represent extinctions in mE, as were measured at the measurement wavelength of 450

TABLE 9

Model B in accordance with example 2 with the
dispensing profiles having been optimized as
shown in FIG. 7
The plate was located in position C as shown in FIG. 3

| Row: | Strips: | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 98 | 97 | 98 | 98 | 11 | 12 | 12 | 11 | 11 | 11 | 12 | 12 |
| B | 99 | 99 | 99 | 99 | 11 | 11 | 12 | 12 | 12 | 11 | 11 | 11 |
| C | 101 | 97 | 97 | 104 | 11 | 11 | 11 | 11 | 11 | 11 | 11 | 11 |
| D | 107 | 99 | 99 | 99 | 11 | 11 | 11 | 11 | 11 | 11 | 11 | 11 |
| E | 99 | 98 | 98 | 98 | 11 | 10 | 11 | 10 | 11 | 11 | 11 | 11 |
| F | 97 | 98 | 98 | 97 | 11 | 11 | 11 | 12 | 11 | 11 | 11 | 11 |
| G | 98 | 98 | 98 | 97 | 11 | 11 | 11 | 11 | 11 | 11 | 11 | 11 |
| H | 98 | 98 | 98 | 98 | 11 | 12 | 12 | 12 | 12 | 12 | 11 | 12 |

Values represent extinctions in mE, as were measured at the measurement wavelength of 450

TABLE 10

Model B in accordance with example 2 with the
dispensing profiles having been optimized as
shown in FIG. 7
The plate was located in position B as shown in FIG. 3

| Row: | Strips: | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 16 | 17 | 16 | 16 | 16 | 16 | 17 | 17 | 17 | 16 | 16 | 16 |
| B | 17 | 17 | 18 | 16 | 16 | 17 | 17 | 17 | 17 | 17 | 17 | 17 |
| C | 15 | 17 | 17 | 16 | 16 | 16 | 16 | 15 | 17 | 17 | 16 | 16 |
| D | 16 | 16 | 16 | 15 | 16 | 16 | 16 | 16 | 16 | 16 | 15 | 16 |
| E | 16 | 15 | 15 | 14 | 15 | 16 | 16 | 18 | 17 | 16 | 15 | 15 |
| F | 12 | 12 | 12 | 12 | 14 | 12 | 12 | 12 | 15 | 12 | 12 | 12 |
| G | 16 | 15 | 16 | 15 | 15 | 16 | 16 | 16 | 19 | 17 | 16 | 16 |
| H | 17 | 17 | 16 | 16 | 16 | 16 | 16 | 16 | 20 | 958 | 17 | 16 |

Values represent extinctions in mE, as were measured at the measurement wavelength of 450

TABLE 11

Model B in accordance with example 2 with the dispensing
profiles having been optimized as shown in FIG. 7
The plate was located in position A as shown in FIG. 3

| Row: | Strips: | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 17 | 18 | 17 | 17 | 17 | 17 | 17 | 17 | 16 | 16 | 17 | 16 |
| B | 17 | 17 | 17 | 17 | 17 | 16 | 16 | 18 | 17 | 16 | 17 | 16 |
| C | 16 | 16 | 16 | 16 | 17 | 16 | 16 | 15 | 16 | 16 | 16 | 16 |
| D | 16 | 16 | 16 | 16 | 17 | 16 | 16 | 16 | 16 | 3000 | 18 | 17 |
| E | 16 | 15 | 16 | 16 | 15 | 15 | 83 | 16 | 15 | 15 | 15 | 18 |
| F | 15 | 15 | 16 | 15 | 15 | 16 | 48 | 16 | 3000 | 16 | 19 | 14 |
| G | 16 | 15 | 16 | 15 | 15 | 15 | 29 | 15 | 65 | 423 | 21 | 14 |
| H | 16 | 16 | 15 | 1443 | 16 | 16 | 31 | 2220 | 1015 | 14 | 20 | 16 |

Values represent extinctions in mE, as were measured at the measurement wavelength of 450

TABLE 12

Model B in accordance with example 2 (after the aspirate and dispensing profiles had been optimized)
The plate was located in position B as shown in FIG. 3

| Row: | Strips: | | | | | | | | | | | |
|------|---|---|---|---|---|---|---|---|---|---|---|---|
|      | 1 | 2 | 3 | 4 | 5 | 6 | 7 | 8 | 9 | 10 | 11 | 12 |
| A | 36 | 37 | 37 | 36 | 35 | 35 | 35 | 35 | 35 | 35 | 37 | 35 |
| B | 35 | 35 | 34 | 35 | 35 | 34 | 35 | 49 | 35 | 35 | 34 | 35 |
| C | 36 | 34 | 36 | 36 | 35 | 35 | 35 | 35 | 34 | 35 | 36 | 35 |
| D | 34 | 35 | 36 | 34 | 35 | 34 | 35 | 34 | 36 | 34 | 34 | 34 |
| E | 33 | 34 | 35 | 35 | 34 | 34 | 35 | 34 | 32 | 34 | 33 | 34 |
| F | 32 | 34 | 34 | 35 | 33 | 33 | 36 | 34 | 33 | 53 | 35 | 34 |
| G | 33 | 33 | 34 | 34 | 34 | 34 | 36 | 35 | 35 | 34 | 33 | 35 |
| H | 33 | 35 | 35 | 34 | 34 | 34 | 37 | 33 | 34 | 34 | 35 | 35 |

Values represent extinctions in mE, as were measured at the measurement wavelength of 450

TABLE 13

Model B in accordance with example 2
The plate was located in position A as shown in FIG. 3

| Row: | Strips: | | | | | | | | | | | |
|------|---|---|---|---|---|---|---|---|---|---|---|---|
|      | 1 | 2 | 3 | 4 | 5 | 6 | 7 | 8 | 9 | 10 | 11 | 12 |
| A | 8 | 7 | 7 | 7 | 4 | 4 | 8 | 6 | 7 | 7 | 7 | 599 |
| B | 7 | 8 | 7 | 8 | 8 | 7 | 8 | 11 | 9 | 7 | 8 | 7 |
| C | 7 | 7 | 7 | 7 | 7 | 7 | 8 | 7 | 7 | 7 | 1052 | 7 |
| D | 8 | 8 | 7 | 7 | 7 | 7 | 8 | 8 | 8 | 7 | 1074 | 7 |
| E | 8 | 7 | 9 | 7 | 7 | 32 | 180 | 7 | 8 | 118 | 49 | 7 |
| F | 7 | 7 | 20 | 7 | 7 | 93 | 185 | 6 | 7 | 122 | 104 | 8 |
| G | 9 | 8 | 32 | 7 | 7 | 165 | 77 | 8 | 7 | 54 | 151 | 8 |
| H | 0 | 6 | 55 | 7 | 5 | 142 | 72 | 687 | 6 | 596 | 297 | 8 |

Values represent extinctions in mE, as were measured at the measurement wavelength of 450

TABLE 14

Model B in accordance with example 2
The plate was located in position B as shown in FIG. 3

| Row: | Strips: | | | | | | | | | | | |
|------|---|---|---|---|---|---|---|---|---|---|---|---|
|      | 1 | 2 | 3 | 4 | 5 | 6 | 7 | 8 | 9 | 10 | 11 | 12 |
| A | 8 | 9 | 8 | 8 | 7 | 8 | 9 | 8 | 7 | 7 | 7 | 8 |
| B | 8 | 7 | 9 | 8 | 9 | 8 | 11 | 8 | 8 | 10 | 9 | 8 |
| C | 8 | 8 | 8 | 8 | 8 | 8 | 8 | 8 | 7 | 8 | 7 | 7 |
| D | 9 | 8 | 8 | 8 | 8 | 8 | 8 | 8 | 8 | 8 | 8 | 8 |
| E | 8 | 8 | 8 | 8 | 8 | 7 | 7 | 8 | 8 | 8 | 8 | 8 |
| F | 8 | 8 | 8 | 8 | 8 | 7 | 8 | 8 | 8 | 8 | 8 | 8 |
| G | 13 | 8 | 8 | 8 | 8 | 8 | 8 | 8 | 8 | 8 | 8 | 7 |
| H | 6 | 8 | 8 | 8 | 7 | 8 | 8 | 8 | 8 | 8 | 8 | 8 |

Values represent extinctions in mE, as were measured at the measurement wavelength of 450

TABLE 15

Model B in accordance with example 2
The plate was located in position C as shown in FIG. 3

| Row: | Strips: | | | | | | | | | | | |
|------|---|---|---|---|---|---|---|---|---|---|---|---|
|      | 1 | 2 | 3 | 4 | 5 | 6 | 7 | 8 | 9 | 10 | 11 | 12 |
| A | 101 | 103 | 103 | 102 | 7 | 7 | 8 | 7 | 6 | 7 | 7 | 8 |
| B | 104 | 102 | 102 | 105 | 8 | 7 | 7 | 8 | 7 | 8 | 8 | 8 |
| C | 103 | 103 | 102 | 103 | 7 | 6 | 7 | 7 | 7 | 7 | 7 | 7 |
| D | 102 | 104 | 104 | 103 | 7 | 7 | 6 | 7 | 7 | 7 | 7 | 7 |
| E | 102 | 102 | 103 | 103 | 7 | 6 | 7 | 7 | 6 | 7 | 15 | 22 |
| F | 102 | 102 | 102 | 104 | 6 | 6 | 5 | 6 | 6 | 6 | 41 | 30 |
| G | 102 | 103 | 102 | 103 | 7 | 7 | 7 | 7 | 7 | 7 | 33 | 22 |
| H | 101 | 104 | 103 | 103 | 7 | 6 | 6 | 7 | 7 | 7 | 29 | 18 |

Values represent extinctions in mE, as were measured at the measurement wavelength of 450

TABLE 16

Enzygnost HBsAg 5.0
(Plate in pos. A with the pipettor profiles having been optimized and with the LWS having been covered)
Testing of 20 pos. samples in positions E1-H3, 71 neg. samples in positions A4-G12 Negative control in positions A1-C1 and positive control in positions D1 and H12 Cutoff = 87 mE, corresponding to = 0.087 OD

| Row: | Strips: | | | | | | | | | | | |
|------|---|---|---|---|---|---|---|---|---|---|---|---|
|      | 1 | 2 | 3 | 4 | 5 | 6 | 7 | 8 | 9 | 10 | 11 | 12 |
| A | 57 | 1111 | 1120 | 21 | 25 | 29 | 23 | 34 | 25 | 20 | 29 | 38 |
| B | 57 | 2826 | 959 | 29 | 24 | 34 | 22 | 36 | 32 | 28 | 30 | 35 |
| C | 55 | 2630 | 2968 | 24 | 29 | 24 | 31 | 24 | 17 | 25 | 27 | 39 |
| D | 1398 | 3000 | 3000 | 27 | 27 | 22 | 48 | 26 | 27 | 22 | 31 | 58 |
| E | 3000 | 3000 | 3000 | 28 | 21 | 24 | 23 | 33 | 23 | 17 | 31 | 28 |
| F | 3000 | 3000 | 3000 | 23 | 24 | 28 | 47 | 33 | 29 | 23 | 38 | 29 |
| G | 3000 | 3000 | 3000 | 22 | 25 | 31 | 24 | 43 | 22 | 57 | 40 | 30 |
| H | 2800 | 2012 | 3000 | 22 | 29 | 28 | 29 | 29 | 31 | 19 | 26 | 1063 |

Values represent extinctions in mE, as were measured at the measurement wavelength of 450

TABLE 17

Enzygnost HIV Integral
(Plate in pos. A with the pipettor profiles having been
optimized and with the FWS having been covered)
Testing of 30 pos. samples in positions E1-H3 and E6-F7,
61 neg. samples in positions A4-D6 and G7-G12
Negative control in positions A1-C1 and positive control
in positions D1 and H12 Cutoff = 510 mE,
corresponding to = 0.5 OD

| | Strips: | | | | | | | | | | | |
|---|---|---|---|---|---|---|---|---|---|---|---|---|
| Row: | 1 | 2 | 3 | 4 | 5 | 6 | 7 | 8 | 9 | 10 | 11 | 12 |
| A | 60 | 2857 | 2863 | 34 | 31 | 38 | 2906 | 34 | 38 | 33 | 33 | 38 |
| B | 62 | 2945 | 2958 | 47 | 38 | 36 | 2983 | 39 | 33 | 36 | 39 | 33 |
| C | 60 | 3000 | 3000 | 36 | 34 | 53 | 3000 | 38 | 43 | 29 | 49 | 39 |
| D | 1877 | 3000 | 3000 | 458 | 34 | 50 | 3000 | 30 | 28 | 33 | 44 | 31 |
| E | 3000 | 3000 | 3000 | 44 | 37 | 3000 | 3000 | 32 | 41 | 37 | 28 | 36 |
| F | 3000 | 3000 | 3000 | 37 | 30 | 3000 | 3000 | 29 | 44 | 27 | 27 | 30 |
| G | 3000 | 3000 | 3000 | 41 | 38 | 3000 | 41 | 30 | 79 | 32 | 30 | 29 |
| H | 3000 | 3000 | 3000 | 32 | 49 | 3000 | 27 | 33 | 34 | 27 | 30 | 1091 |

Values represent extinctions in mE, as were measured at the measurement wavelength of 450

TABLE 18

Enzygnost HBsAg 5.0 (Position A)
Testing of 20 pos. samples in positions E1-H3, 71 neg. samples
in positions A4-G12 Negative control in positions A1-C1 and
positive control in positions D1 and H12
Cutoff = 105 mE, corresponding to = 0.105 OD

| | Strips: | | | | | | | | | | | |
|---|---|---|---|---|---|---|---|---|---|---|---|---|
| Row: | 1 | 2 | 3 | 4 | 5 | 6 | 7 | 8 | 9 | 10 | 11 | 12 |
| A | 59 | 2877 | 2855 | 76 | 68 | 68 | 69 | 62 | 62 | 71 | 64 | 62 |
| B | 57 | 2936 | 2946 | 82 | 69 | 71 | 74 | 82 | 69 | 71 | 70 | 81 |
| C | 49 | 3000 | 3000 | 77 | 73 | 69 | 70 | 67 | 65 | 77 | 67 | 67 |
| D | 2954 | 3000 | 3000 | 68 | 70 | 75 | 69 | 70 | 67 | 68 | 77 | 72 |
| E | 3000 | 3000 | 3000 | 74 | 89 | 68 | 71 | 68 | 77 | 73 | 74 | 73 |
| F | 3000 | 3000 | 3000 | 77 | 74 | 70 | 78 | 71 | 72 | 71 | 70 | 74 |
| G | 3000 | 3000 | 3000 | 127 | 68 | 68 | 73 | 70 | 71 | 75 | 69 | 78 |
| H | 3000 | 3000 | 3000 | 62 | 60 | 57 | 57 | 68 | 69 | 67 | 66 | 969 |

Values represent extinctions in mE, as were measured at the measurement wavelength of 450

TABLE 19

Enzygnost HBsAg 5.0 (samples dispensed using the Tecan RSP 150)
Testing of 18 pos. samples in positions E1-H3, 71 neg. samples in
positions A4-G12 Negative control in positions A1-C1 and positive
control in positions D1 and H12 Cutoff = 96 mE, corresponding
to = 0.096 OD

| | Strips: | | | | | | | | | | | |
|---|---|---|---|---|---|---|---|---|---|---|---|---|
| Row: | 1 | 2 | 3 | 4 | 5 | 6 | 7 | 8 | 9 | 10 | 11 | 12 |
| A | 43 | empty | 2380 | 16 | 23 | 20 | 21 | 17 | 28 | 18 | 22 | 21 |
| B | 33 | 3000 | 3000 | 40 | 25 | 33 | 22 | 21 | 17 | 18 | 16 | 19 |
| C | 62 | 2367 | 3000 | 203 | 25 | 19 | 27 | 16 | 18 | 21 | 15 | 19 |
| D | 1758 | 3000 | 3000 | 21 | 24 | 22 | 16 | 22 | 20 | 16 | 20 | 21 |
| E | 3000 | 3000 | 3000 | 22 | 22 | 25 | 38 | 24 | 20 | 19 | 20 | 23 |
| F | 3000 | 3000 | 3000 | 460 | 26 | 28 | 23 | 32 | 22 | 23 | 21 | 22 |
| G | 3000 | 3000 | 3000 | 1264 | 24 | 29 | 22 | 25 | 25 | 30 | 26 | 28 |
| H | empty | 3000 | 3000 | 29 | 30 | 25 | 28 | 23 | 25 | 27 | 24 | 1535 |

Values represent extinctions in mE, as were measured at the measurement wavelength of 450

TABLE 20

Enzygnost HBsAg 5.0 (samples dispensed using the Tecan RSP 150)
Testing of 18 pos. samples in positions E1-H3, 71 neg. samples in
positions A4-G12 Negative control in positions A1 and C1 and
positive control in positions D1 and H12
Cutoff = 80 mE, corresponding to = 0.080 OD

| | Strips: | | | | | | | | | | | |
|---|---|---|---|---|---|---|---|---|---|---|---|---|
| Row: | 1 | 2 | 3 | 4 | 5 | 6 | 7 | 8 | 9 | 10 | 11 | 12 |
| A | 32 | empty | 2387 | 15 | 25 | 18 | 20 | 16 | 24 | 16 | 25 | 21 |
| B | empty | 3000 | 2633 | 58 | 17 | 20 | 19 | 17 | 15 | 18 | 18 | 18 |
| C | 27 | 2586 | 3000 | 18 | 25 | 18 | 24 | 19 | 16 | 18 | 15 | 22 |
| D | 1693 | 3000 | 3000 | 19 | 24 | 22 | 17 | 24 | 19 | 15 | 23 | 21 |
| E | 3000 | 3000 | 3000 | 22 | 21 | 22 | 43 | 23 | 20 | 19 | 22 | 24 |
| F | 3000 | 3000 | 3000 | 28 | 26 | 25 | 23 | 33 | 18 | 24 | 22 | 25 |
| G | 3000 | 3000 | 3000 | 30 | 24 | 26 | 250 | 26 | 23 | 25 | 26 | 34 |
| H | empty | 2943 | 3000 | 28 | 30 | 22 | 25 | 24 | 20 | 28 | 27 | 1717 |

Values represent extinctions in mE, as were measured at the measurement wavelength of 450

TABLE 21

Enzygnost Anti-HBs II
Testing of 20 pos. samples in positions F1-A4, 70 neg. samples in
positions B4-G12 Negative control in positions A1-D1 and positive
control in positions E1 and H12 Cutoff = 136 mE,
corresponding to = 0.136 OD

| | Strips: | | | | | | | | | | | |
|---|---|---|---|---|---|---|---|---|---|---|---|---|
| Row: | 1 | 2 | 3 | 4 | 5 | 6 | 7 | 8 | 9 | 10 | 11 | 12 |
| A | 58 | 3000 | 3000 | 3000 | 74 | 53 | 77 | 45 | 76 | 67 | 50 | 68 |
| B | 57 | 3000 | 3000 | 58 | 53 | 56 | 64 | 67 | 64 | 86 | 98 | 100 |
| C | 52 | 3000 | 3000 | 62 | 57 | 87 | 99 | 92 | 55 | 79 | 62 | 85 |
| D | 62 | 3000 | 3000 | 81 | 89 | 63 | 72 | 81 | 61 | 51 | 73 | 71 |
| E | 1346 | 3000 | 3000 | 56 | 87 | 50 | 100 | 49 | 99 | 66 | 68 | 57 |
| F | 3000 | 3000 | 3000 | 72 | 69 | 91 | 68 | 56 | 49 | 73 | 59 | 66 |
| G | 3000 | 3000 | 3000 | 90 | 91 | 57 | 59 | 64 | 66 | 48 | 51 | 63 |
| H | 3000 | 3000 | 3000 | 81 | 61 | 53 | 97 | 71 | 58 | 66 | 67 | 1173 |

Values represent extinctions in mE, as were measured at the measurement wavelength of 450

TABLE 22

Enzygnost Anti-HAV (test principle: competition)
Testing of 20 pos. samples in positions F1-A4, 70 neg. samples in
positions B4–G12 Negative control in positions A1–D1 and positive control
in positions E1 and H12 Cutoff = 672 mE, corresponding to = 0.672 OD

| | Strips: | | | | | | | | | | | |
|---|---|---|---|---|---|---|---|---|---|---|---|---|
| Row: | 1 | 2 | 3 | 4 | 5 | 6 | 7 | 8 | 9 | 10 | 11 | 12 |
| A | 1481 | 34 | 50 | 31 | 1252 | 1514 | 1422 | 1340 | 1256 | 1465 | 1424 | 1387 |
| B | 1243 | 31 | 27 | 1476 | 1468 | 1355 | 1387 | 1388 | 1434 | 1422 | 1228 | 1439 |
| C | 1304 | 47 | 157 | 1501 | 1384 | 1333 | 1452 | 1245 | 1366 | 1345 | 1615 | 1313 |
| D | 1354 | 29 | 99 | 1210 | 1131 | 1185 | 1374 | 1392 | 1472 | 1266 | 1532 | 1298 |
| E | 177 | 27 | 128 | 1439 | 1423 | 1381 | 1123 | 1102 | 1368 | 1421 | 1557 | 1401 |
| F | 40 | 27 | 53 | 1435 | 1355 | 1395 | 1513 | 1327 | 1525 | 1555 | 1477 | 1523 |
| G | 34 | 47 | 28 | 1454 | 1135 | 1253 | 1405 | 1268 | 1398 | 1199 | 1456 | 1333 |
| H | 98 | 25 | 29 | 1414 | 1293 | 1361 | 1360 | 1250 | 1436 | 1367 | 1399 | 159 |

Values represent extinctions in mE, as were measured at the measurement wavelength of 450

TABLE 23

Enzygnost HBe monoclonal (test principle: competition)
Testing of 26 pos. samples in positions F1–G4 and 64 neg. samples in positions H4–G12
The negative control is located in positions A1–D1 and the positive control in positions
E1 and H12 Cutoff = 902 mE, corresponding to = 0.902 OD

| | Strips: | | | | | | | | | | | |
|---|---|---|---|---|---|---|---|---|---|---|---|---|
| Row: | 1 | 2 | 3 | 4 | 5 | 6 | 7 | 8 | 9 | 10 | 11 | 12 |
| A | 1867 | 13 | 17 | 15 | 1672 | 1670 | 1689 | 1651 | 1626 | 1605 | 1606 | 1628 |
| B | 1851 | 13 | 15 | 13 | 1628 | 1701 | 1717 | 1649 | 1634 | 1632 | 1568 | 1666 |
| C | 1713 | 12 | 14 | 14 | 1701 | 1649 | 1633 | 1653 | 1602 | 1619 | 1650 | 1687 |
| D | 1792 | 14 | 21 | 408 | 1688 | 1770 | 1700 | 1657 | 1564 | 1618 | 1639 | 1671 |
| E | 17 | 17 | 14 | 14 | 1655 | 1650 | 1740 | 1570 | 1679 | 1521 | 1567 | 1639 |
| F | 14 | 23 | 15 | 15 | 1622 | 1615 | 1648 | 1666 | 1555 | 1685 | 1608 | 1694 |
| G | 22 | 22 | 21 | 17 | 1317 | 1715 | 1607 | 1645 | 1538 | 1544 | 1592 | 1616 |
| H | 18 | 15 | 16 | 1639 | 1684 | 1691 | 1674 | 1533 | 1578 | 1667 | 1710 | 18 |

Values represent extinctions in mE, as were measured at the measurement wavelength of 450

The invention claimed is:

1. A method for reducing contamination of empty reaction vessels, or of reaction vessels which are already charged with an analyte-free sample material or a sample material which contains a low concentration of analyte, within an arrangement of reaction vessels which are located in spatial proximity to each other while samples or reagents are pipetted using an automated sample dispenser having liquid uptake (aspirate profile) and liquid release (dispense profile) parameters, the method comprising using an enzyme/dye test to initially establish the extent of the contamination by:
    adding an enzyme solution to the reaction vessels in a first constituent region of the spatial arrangement,
    adding a suitable chromogen/substrate reagent, which, on contact with the enzyme, induces a color reaction, to the reaction vessels in a second constituent region of the spatial arrangement,
    ascertaining possible contaminations by determining color development in the reaction vessels; and
    subsequently modifying a rate of the liquid uptake (aspirate profile) and the liquid release (dispense profile) parameters of the automatic sample dispenser such that a number or an intensity of color in the reaction vessels marked by the color development is reduced.

2. The method as claimed in claim 1, wherein adding the enzyme solution to the reaction vessels includes adding the enzyme solution to wells in a microtitration plate.

3. The method as claimed in claim 2, wherein:
    the automatic sample dispenser is part of a fully automated analyzer;
    the arrangement of reaction vessels which are located in spatial proximity to each other includes a linear arrangement, which lies in a horizontal plane, of four microtitration plates in a sequence including: a position A, a position B, a position C, and a position D;
    a liquid waste station is located in immediate proximity to the position A in an approximate extension of an imaginary line from the position D to the position A;
    wherein adding the enzyme solution includes adding the enzyme solution to the first constituent region of the microtitration plates in the positions A to D; and
    ascertaining the possible contaminations includes ascertaining whether the contaminations are emanating from the liquid waste station.

4. The method as claimed in claim 3, further comprising:
    covering the liquid waste station with an upper covering having an aperture, wherein the aperture is sized to provide optimal protection against splashes from the liquid waste station while permitting release of excess sample volume through the aperture into the liquid waste station such that no liquid inadvertently comes into contact with an edge of the aperture.

5. The method as claimed in claim 4, further comprising:
    separating the liquid waste station from the microtitration plates.

6. The method as claimed in claim 4, wherein separating the liquid waste station from the microtitration plates includes installing a mechanical protective device between the liquid waste station and the positions of the coated microtitration plates, thereby preventing the contaminations.

* * * * *